(12) United States Patent
Jones et al.

(10) Patent No.: US 12,011,355 B2
(45) Date of Patent: Jun. 18, 2024

(54) LASER-PRODUCED POROUS SURFACE

(71) Applicants: Howmedica Osteonics Corp., Mahwah, NJ (US); The University Of Liverpool, Liverpool (GB)

(72) Inventors: Eric Jones, Limerick (IE); Christopher J. Sutcliffe, Liverpool (GB); Robin Stamp, Montclair, NJ (US)

(73) Assignees: Howmedica Osteonics Corp., Mahwah, NJ (US); The University Of Liverpool, Liverpool (GB)

( * ) Notice: Subject to any disclaimer, the term of this patent is extended or adjusted under 35 U.S.C. 154(b) by 0 days.

(21) Appl. No.: 18/420,381

(22) Filed: Jan. 23, 2024

(65) Prior Publication Data
US 2024/0156605 A1    May 16, 2024

Related U.S. Application Data

(63) Continuation of application No. 16/900,219, filed on Jun. 12, 2020, now Pat. No. 11,918,474, which is a
(Continued)

(51) Int. Cl.
*A61F 2/30*    (2006.01)
*A61F 2/32*    (2006.01)
(Continued)

(52) U.S. Cl.
CPC ............ *A61F 2/30907* (2013.01); *A61F 2/30* (2013.01); *A61L 27/306* (2013.01); *A61L 27/56* (2013.01);
(Continued)

(58) Field of Classification Search
CPC .. A61L 27/56; A61F 2/30756; A61F 2/30767; A61F 2/3094; A61F 2/32;
(Continued)

(56) References Cited

U.S. PATENT DOCUMENTS

| 14,403 A | 3/1856 | Brown et al. |
| 222,687 A | 12/1879 | Fresco |

(Continued)

FOREIGN PATENT DOCUMENTS

| CA | 2295896 A1 | 7/2000 |
| CA | 2448592 A1 | 5/2004 |

(Continued)

OTHER PUBLICATIONS

Hollander et al., Structural mechanical and in vitro characterization of individually structured Ti-A1-4V produces by direct layer forming, Biomaterials, pp. 1-9, 2005.
(Continued)

*Primary Examiner* — Seema Mathew
(74) *Attorney, Agent, or Firm* — Lerner David LLP

(57) ABSTRACT

A method of forming an implant having a porous tissue ingrowth structure and a bearing support structure. The method includes depositing a first layer of a metal powder onto a substrate, scanning a laser beam over the powder so as to sinter the metal powder at predetermined locations, depositing at least one layer of the metal powder onto the first layer and repeating the scanning of the laser beam.

20 Claims, 20 Drawing Sheets

Related U.S. Application Data continuation of application No. 15/788,304, filed on Oct. 19, 2017, now Pat. No. 10,716,673, which is a continuation of application No. 14/276,483, filed on May 13, 2014, now Pat. No. 10,398,559, which is a continuation of application No. 11/295,008, filed on Dec. 6, 2005, now Pat. No. 8,728,387.

(51) Int. Cl.

| | | |
|---|---|---|
| *A61L 27/30* | (2006.01) | |
| *A61L 27/56* | (2006.01) | |
| *B22F 3/11* | (2006.01) | |
| *B22F 5/10* | (2006.01) | |
| *B22F 10/28* | (2021.01) | |
| *B22F 10/38* | (2021.01) | |
| *B23K 26/382* | (2014.01) | |
| *B29C 37/00* | (2006.01) | |
| *B29C 45/14* | (2006.01) | |
| *B33Y 70/00* | (2020.01) | |
| *B33Y 80/00* | (2015.01) | |
| *C23C 4/02* | (2006.01) | |
| *C23C 4/18* | (2006.01) | |
| *C23C 24/10* | (2006.01) | |
| *C23C 26/02* | (2006.01) | |
| *A61F 2/34* | (2006.01) | |
| *A61F 2/36* | (2006.01) | |
| *A61F 2/38* | (2006.01) | |
| *B22F 10/32* | (2021.01) | |
| *B22F 10/36* | (2021.01) | |
| *B22F 10/366* | (2021.01) | |
| *B22F 10/62* | (2021.01) | |
| *B22F 10/64* | (2021.01) | |
| *B22F 12/41* | (2021.01) | |
| *B29L 31/00* | (2006.01) | |
| *B33Y 10/00* | (2015.01) | |

(52) U.S. Cl.
CPC .............. *B22F 3/1109* (2013.01); *B22F 5/10* (2013.01); *B22F 10/28* (2021.01); *B22F 10/38* (2021.01); *B23K 26/382* (2015.10); *B29C 37/0082* (2013.01); *B29C 45/14311* (2013.01); *B33Y 70/00* (2014.12); *B33Y 80/00* (2014.12); *C23C 4/02* (2013.01); *C23C 4/18* (2013.01); *C23C 24/10* (2013.01); *C23C 26/02* (2013.01); *A61F 2002/30011* (2013.01); *A61F 2002/30199* (2013.01); *A61F 2002/30243* (2013.01); *A61F 2002/30261* (2013.01); *A61F 2002/3028* (2013.01); *A61F 2002/30329* (2013.01); *A61F 2002/30593* (2013.01); *A61F 2002/30594* (2013.01); *A61F 2/30756* (2013.01); *A61F 2/30767* (2013.01); *A61F 2002/30915* (2013.01); *A61F 2002/3092* (2013.01); *A61F 2/3094* (2013.01); *A61F 2/30965* (2013.01); *A61F 2002/30968* (2013.01); *A61F 2002/3097* (2013.01); *A61F 2002/30971* (2013.01); *A61F 2/32* (2013.01); *A61F 2002/3401* (2013.01); *A61F 2002/3425* (2013.01); *A61F 2/36* (2013.01); *A61F 2/3877* (2013.01); *A61F 2220/0025* (2013.01); *A61F 2230/0063* (2013.01); *A61F 2230/0071* (2013.01); *A61F 2230/0082* (2013.01); *A61F 2250/0023* (2013.01); *B22F 10/32* (2021.01); *B22F 10/36* (2021.01); *B22F 10/366* (2021.01); *B22F 10/62* (2021.01); *B22F 10/64* (2021.01); *B22F 12/41* (2021.01); *B22F 2999/00* (2013.01); *B29C 2045/14327* (2013.01); *B29L 2031/7532* (2013.01); *B33Y 10/00* (2014.12); *Y02P 10/25* (2015.11)

(58) Field of Classification Search
CPC ...... A61F 2002/3097; A61F 2002/3092; A61F 2002/30971; A61F 2002/30011; A61F 2002/30199; A61F 2/36; A61F 2/30; A61F 2/3859; A61F 2/34; A61F 2/389
See application file for complete search history.

(56) References Cited

U.S. PATENT DOCUMENTS

| | | | |
|---|---|---|---|
| 2,373,769 A | 4/1945 | Macy | |
| 3,520,099 A | 7/1970 | Mattes | |
| 3,556,918 A | 1/1971 | Lemelson | |
| 3,605,123 A | 9/1971 | Pratt et al. | |
| 3,806,961 A | 4/1974 | Muller | |
| 3,816,855 A | 6/1974 | Saleh | |
| 3,826,054 A | 7/1974 | Culpepper, Jr. | |
| 3,852,045 A * | 12/1974 | Wheeler | A61F 2/28 606/76 |
| 3,855,638 A * | 12/1974 | Pilliar | A61F 2/30 433/173 |
| 3,890,107 A * | 6/1975 | White | A61F 2/28 521/149 |
| 3,906,550 A | 9/1975 | Rostoker et al. | |
| 4,047,349 A | 9/1977 | Aguilar, Jr. | |
| 4,073,999 A * | 2/1978 | Bryan | C04B 38/02 606/76 |
| 4,085,466 A | 4/1978 | Goodfellow et al. | |
| 4,117,302 A | 9/1978 | Earle et al. | |
| 4,154,040 A | 5/1979 | Pace | |
| 4,164,794 A * | 8/1979 | Spector | A61C 8/0016 606/76 |
| 4,179,485 A * | 12/1979 | Tritten | C04B 35/10 264/642 |
| 4,202,055 A | 5/1980 | Reiner et al. | |
| 4,218,494 A * | 8/1980 | Belmondo | C22C 32/0052 29/888.074 |
| 4,247,508 A | 1/1981 | Housholder | |
| 4,259,072 A | 3/1981 | Hirabayashi et al. | |
| 4,305,340 A | 12/1981 | Iwaki et al. | |
| 4,344,193 A | 8/1982 | Kenny | |
| 4,385,404 A | 5/1983 | Sully et al. | |
| 4,444,818 A | 4/1984 | Tominaga et al. | |
| 4,474,861 A | 10/1984 | Ecer | |
| 4,479,271 A | 10/1984 | Bolesky et al. | |
| 4,502,161 A | 3/1985 | Wall | |
| 4,513,045 A | 4/1985 | Bondoc et al. | |
| 4,542,539 A | 9/1985 | Rowe, Jr. et al. | |
| 4,543,158 A | 9/1985 | Bondoc et al. | |
| 4,550,448 A | 11/1985 | Kenna | |
| 4,636,219 A | 1/1987 | Pratt et al. | |
| 4,644,942 A | 2/1987 | Sump | |
| 4,659,331 A | 4/1987 | Matthews et al. | |
| 4,673,408 A | 6/1987 | Grobbelaar | |
| 4,673,409 A | 6/1987 | Van Kampen | |
| 4,714,473 A | 12/1987 | Bloebaum | |
| 4,714,474 A | 12/1987 | Brooks, Jr. et al. | |
| 4,719,908 A | 1/1988 | Averill et al. | |
| 4,766,029 A | 8/1988 | Brock et al. | |
| 4,863,538 A | 9/1989 | Deckard | |
| 4,944,756 A | 7/1990 | Kenna | |
| 4,944,817 A | 7/1990 | Bourell et al. | |
| 4,957,819 A | 9/1990 | Kawahara et al. | |
| 4,961,154 A | 10/1990 | Pomerantz et al. | |
| 4,969,302 A | 11/1990 | Coggan et al. | |
| 4,969,907 A | 11/1990 | Koch et al. | |
| 4,969,910 A | 11/1990 | Frey et al. | |
| 4,976,738 A | 12/1990 | Frey et al. | |
| 4,978,355 A | 12/1990 | Frey et al. | |
| 4,990,163 A | 2/1991 | Ducheyne et al. | |
| 4,997,445 A | 3/1991 | Hodorek | |
| 5,002,572 A | 3/1991 | Picha | |
| 5,004,476 A | 4/1991 | Cook | |
| 5,017,753 A | 5/1991 | Deckard | |

(56) References Cited

U.S. PATENT DOCUMENTS

| | | |
|---|---|---|
| 5,024,670 A | 6/1991 | Smith et al. |
| 5,031,120 A | 7/1991 | Pomerantz et al. |
| 5,034,186 A | 7/1991 | Shimamune et al. |
| 5,053,090 A | 10/1991 | Beaman et al. |
| 5,067,964 A | 11/1991 | Richmond et al. |
| 5,076,869 A | 12/1991 | Bourell et al. |
| 5,080,674 A | 1/1992 | Jacobs et al. |
| 5,090,174 A | 2/1992 | Fragale |
| 5,108,432 A | 4/1992 | Gustavson |
| 5,108,441 A | 4/1992 | McDowell |
| 5,147,402 A | 9/1992 | Bohler et al. |
| 5,150,304 A | 9/1992 | Berchem et al. |
| 5,155,324 A | 10/1992 | Deckard et al. |
| 5,158,574 A | 10/1992 | Stone |
| 5,171,282 A | 12/1992 | Pequignot |
| 5,176,710 A | 1/1993 | Hahn et al. |
| 5,192,328 A | 3/1993 | Winters |
| 5,219,362 A | 6/1993 | Tuke et al. |
| 5,274,565 A | 12/1993 | Reuben |
| 5,282,861 A * | 2/1994 | Kaplan ............... B22F 3/114 623/23.51 |
| 5,282,870 A | 2/1994 | Moser et al. |
| 5,287,435 A | 2/1994 | Cohen et al. |
| 5,298,115 A | 3/1994 | Leonard |
| 5,314,478 A * | 5/1994 | Oka .................. A61F 2/3603 623/14.12 |
| 5,323,954 A | 6/1994 | Shetty et al. |
| 5,336,518 A | 8/1994 | Narayanan et al. |
| 5,352,405 A | 10/1994 | Beaman et al. |
| 5,356,433 A | 10/1994 | Rowland et al. |
| 5,358,529 A | 10/1994 | Davidson |
| 5,368,602 A | 11/1994 | de la Torre |
| 5,370,692 A | 12/1994 | Fink et al. |
| 5,380,328 A * | 1/1995 | Morgan ............. A61F 2/30965 606/70 |
| 5,386,500 A | 1/1995 | Pomerantz et al. |
| 5,397,359 A | 3/1995 | Mittelmeier et al. |
| 5,398,193 A | 3/1995 | deAngelis |
| 5,425,210 A | 6/1995 | Zafir |
| 5,443,510 A * | 8/1995 | Shetty ................ A61L 27/06 623/901 |
| 5,443,518 A | 8/1995 | Insall |
| 5,461,839 A | 10/1995 | Beck |
| 5,486,599 A | 1/1996 | Saunders et al. |
| 5,489,306 A | 2/1996 | Gorski |
| 5,490,962 A | 2/1996 | Cima et al. |
| 5,496,372 A | 3/1996 | Hamamoto et al. |
| 5,504,300 A * | 4/1996 | Devanathan ........ A61F 2/30907 219/121.84 |
| 5,507,815 A | 4/1996 | Wagner et al. |
| 5,510,066 A | 4/1996 | Fink et al. |
| 5,514,183 A | 5/1996 | Epstein et al. |
| 5,518,680 A * | 5/1996 | Cima .................. A61F 2/02 264/41 |
| 5,526,627 A | 6/1996 | Beck |
| 5,549,123 A * | 8/1996 | Okuyama ............. A61L 27/10 433/201.1 |
| 5,549,700 A | 8/1996 | Graham et al. |
| 5,571,185 A | 11/1996 | Schug |
| 5,571,196 A | 11/1996 | Stein |
| 5,580,353 A | 12/1996 | Mendes et al. |
| 5,609,646 A | 3/1997 | Field et al. |
| 5,616,294 A | 4/1997 | Deckard |
| 5,624,463 A | 4/1997 | Stone et al. |
| 5,632,745 A | 5/1997 | Schwartz |
| 5,640,667 A | 6/1997 | Freitag et al. |
| 5,648,450 A | 7/1997 | Dickens, Jr. et al. |
| 5,665,118 A | 9/1997 | LaSalle et al. |
| 5,681,354 A | 10/1997 | Eckhoff |
| 5,702,448 A | 12/1997 | Buechel et al. |
| 5,714,103 A | 2/1998 | Bauer et al. |
| 5,716,358 A | 2/1998 | Ochoa et al. |
| 5,728,162 A | 3/1998 | Eckhoff |
| 5,729,946 A | 3/1998 | Beck |
| 5,735,903 A | 4/1998 | Li et al. |
| 5,749,874 A | 5/1998 | Schwartz |
| 5,768,134 A | 6/1998 | Swaelens et al. |
| 5,769,092 A | 6/1998 | Williamson, Jr. |
| 5,769,899 A | 6/1998 | Schwartz et al. |
| 5,773,789 A | 6/1998 | Devanathan et al. |
| 5,776,201 A | 7/1998 | Colleran et al. |
| 5,782,908 A | 7/1998 | Cahalan et al. |
| 5,795,353 A | 8/1998 | Felt |
| 5,798,924 A | 8/1998 | Eufinger et al. |
| 5,824,098 A | 10/1998 | Stein |
| 5,824,102 A | 10/1998 | Buscayret |
| 5,839,247 A | 11/1998 | Beck |
| 5,857,303 A | 1/1999 | Beck et al. |
| 5,866,113 A * | 2/1999 | Hendriks ............. A61L 31/10 424/78.17 |
| 5,879,387 A | 3/1999 | Jones et al. |
| 5,879,398 A | 3/1999 | Swarts et al. |
| 5,928,285 A | 7/1999 | Bigliani et al. |
| 5,973,222 A | 10/1999 | Devanathan et al. |
| 5,987,838 A | 11/1999 | Beck |
| 5,989,472 A | 11/1999 | Ashby et al. |
| 6,013,855 A | 1/2000 | McPherson et al. |
| 6,042,774 A | 3/2000 | Wilkening et al. |
| 6,045,581 A | 4/2000 | Burkinshaw |
| 6,046,426 A | 4/2000 | Jeantette et al. |
| 6,049,054 A | 4/2000 | Panchison et al. |
| 6,077,989 A | 6/2000 | Kandel et al. |
| 6,087,553 A | 7/2000 | Cohen et al. |
| 6,096,043 A | 8/2000 | Techiera et al. |
| 6,112,109 A | 8/2000 | D'Urso |
| 6,128,866 A | 10/2000 | Wearne |
| 6,132,468 A | 10/2000 | Mansmann |
| 6,139,585 A | 10/2000 | Li |
| 6,149,688 A | 11/2000 | Brosnahan et al. |
| 6,149,689 A | 11/2000 | Grundei |
| 6,164,032 A | 12/2000 | Beck |
| 6,171,340 B1 | 1/2001 | McDowell |
| 6,190,407 B1 | 2/2001 | Ogle et al. |
| 6,206,924 B1 * | 3/2001 | Timm .................. A61F 2/28 623/17.11 |
| 6,206,927 B1 | 3/2001 | Fell et al. |
| 6,209,621 B1 | 4/2001 | Treacy |
| 6,215,093 B1 | 4/2001 | Meiners et al. |
| 6,217,615 B1 | 4/2001 | Sioshansi et al. |
| 6,248,131 B1 | 6/2001 | Felt et al. |
| 6,251,143 B1 | 6/2001 | Schwartz et al. |
| 6,254,639 B1 | 7/2001 | Peckitt |
| 6,261,322 B1 * | 7/2001 | Despres, III ............ A61P 19/00 427/2.27 |
| 6,261,493 B1 | 7/2001 | Gaylo et al. |
| 6,280,478 B1 | 8/2001 | Richter et al. |
| 6,283,997 B1 | 9/2001 | Garg et al. |
| 6,290,726 B1 | 9/2001 | Pope et al. |
| 6,299,645 B1 | 10/2001 | Ogden |
| 6,344,061 B1 | 2/2002 | Leitao et al. |
| 6,350,284 B1 | 2/2002 | Tormala et al. |
| 6,355,086 B2 | 3/2002 | Brown et al. |
| 6,368,354 B2 | 4/2002 | Burstein et al. |
| 6,370,382 B1 | 4/2002 | Kang et al. |
| 6,371,958 B1 | 4/2002 | Overaker |
| 6,379,816 B1 | 4/2002 | De Loose et al. |
| 6,385,585 B1 | 5/2002 | Jonsson et al. |
| 6,395,327 B1 * | 5/2002 | Shetty ................ C23C 24/08 427/247 |
| 6,406,497 B2 | 6/2002 | Takei |
| 6,415,574 B2 | 7/2002 | Beck |
| 6,454,811 B1 | 9/2002 | Sherwood et al. |
| 6,476,343 B2 | 11/2002 | Keicher et al. |
| 6,482,209 B1 | 11/2002 | Engh et al. |
| 6,494,914 B2 | 12/2002 | Brown et al. |
| 6,497,728 B2 | 12/2002 | Yong |
| 6,520,996 B1 | 2/2003 | Manasas et al. |
| 6,530,951 B1 | 3/2003 | Bates et al. |
| 6,551,608 B2 | 4/2003 | Yao |
| 6,558,421 B1 | 5/2003 | Fell et al. |
| 6,582,715 B1 | 6/2003 | Barry et al. |
| 6,589,283 B1 | 7/2003 | Metzger et al. |
| 6,592,598 B2 | 7/2003 | Vibe-Hansen et al. |

(56) References Cited

U.S. PATENT DOCUMENTS

| | | | |
|---|---|---|---|
| 6,599,301 B2 | 7/2003 | Vibe-Hansen et al. | |
| 6,599,322 B1 | 7/2003 | Amrich et al. | |
| 6,599,323 B2* | 7/2003 | Melican | A61L 31/127 |
| | | | 623/23.72 |
| 6,610,067 B2 | 8/2003 | Tallarida et al. | |
| 6,626,945 B2 | 9/2003 | Simon et al. | |
| 6,632,246 B1 | 10/2003 | Simon et al. | |
| 6,652,246 B1 | 11/2003 | Lin et al. | |
| 6,652,587 B2 | 11/2003 | Felt et al. | |
| 6,676,892 B2 | 1/2004 | Das et al. | |
| 6,679,917 B2 | 1/2004 | Ek | |
| 6,682,567 B1* | 1/2004 | Schroeder | A61F 2/4609 |
| | | | 623/22.24 |
| 6,686,437 B2 | 2/2004 | Buchman et al. | |
| 6,699,252 B2 | 3/2004 | Farr, II et al. | |
| 6,702,848 B1* | 3/2004 | Zilla | A61F 2/06 |
| | | | 623/1.39 |
| 6,709,462 B2* | 3/2004 | Hanssen | A61F 2/34 |
| | | | 623/22.34 |
| 6,712,822 B2 | 3/2004 | Re et al. | |
| 6,712,856 B1 | 3/2004 | Carignan et al. | |
| 6,716,957 B2 | 4/2004 | Tunc | |
| 6,743,232 B2 | 6/2004 | Overaker et al. | |
| 6,770,099 B2 | 8/2004 | Andriacchi et al. | |
| 6,772,026 B2 | 8/2004 | Bradbury et al. | |
| 6,802,864 B2 | 10/2004 | Tornier | |
| 6,811,569 B1* | 11/2004 | Afriat | A61F 2/34 |
| | | | 623/22.32 |
| 6,843,807 B1* | 1/2005 | Boyce | A61B 17/7062 |
| | | | 523/113 |
| 6,846,329 B2 | 1/2005 | McMinn | |
| 6,850,125 B2 | 2/2005 | Norman et al. | |
| 6,852,125 B2 | 2/2005 | Simon et al. | |
| 6,855,165 B2 | 2/2005 | Fell et al. | |
| 6,863,689 B2 | 3/2005 | Ralph et al. | |
| 6,866,684 B2 | 3/2005 | Fell et al. | |
| 6,893,463 B2 | 5/2005 | Fell et al. | |
| 6,911,044 B2 | 6/2005 | Fell et al. | |
| 6,916,341 B2 | 7/2005 | Rolston | |
| 6,921,264 B2 | 7/2005 | Mayer et al. | |
| 6,923,831 B2 | 8/2005 | Fell et al. | |
| 6,932,610 B2 | 8/2005 | Ono et al. | |
| 6,966,932 B1 | 11/2005 | Schroeder | |
| 6,993,406 B1 | 1/2006 | Cesarano, III et al. | |
| 7,051,417 B2 | 5/2006 | Michelson | |
| 7,168,283 B2 | 1/2007 | Van Note et al. | |
| 7,294,149 B2 | 11/2007 | Hozack et al. | |
| 7,332,537 B2 | 2/2008 | Bredt et al. | |
| 7,388,972 B2 | 6/2008 | Kitson | |
| 7,465,318 B2 | 12/2008 | Sennett et al. | |
| 7,494,507 B2 | 2/2009 | Dixon et al. | |
| 7,497,876 B2 | 3/2009 | Tuke et al. | |
| 7,521,017 B2 | 4/2009 | Kunze et al. | |
| 7,563,284 B2 | 7/2009 | Coppes et al. | |
| 7,597,715 B2 | 10/2009 | Brown et al. | |
| 7,632,575 B2* | 12/2009 | Justin | C23C 26/00 |
| | | | 427/586 |
| 7,637,942 B2 | 12/2009 | Mangiardi et al. | |
| 7,655,047 B2* | 2/2010 | Swords | A61F 2/30965 |
| | | | 623/23.54 |
| 7,674,517 B2 | 3/2010 | Ramsey et al. | |
| 7,718,109 B2 | 5/2010 | Robb et al. | |
| 7,747,305 B2 | 6/2010 | Dean et al. | |
| 7,779,890 B2 | 8/2010 | Frasier et al. | |
| 7,875,083 B2 | 1/2011 | Sudmann | |
| 7,879,275 B2 | 2/2011 | Smith et al. | |
| 7,922,765 B2 | 4/2011 | Reiley | |
| 7,931,931 B2* | 4/2011 | Yan | A61L 31/146 |
| | | | 427/205 |
| 8,029,575 B2 | 10/2011 | Borden | |
| 8,066,770 B2 | 11/2011 | Rivard et al. | |
| 8,090,540 B2 | 1/2012 | Leo et al. | |
| 8,247,333 B2 | 8/2012 | Sypeck et al. | |
| 8,292,967 B2 | 10/2012 | Brown et al. | |
| 8,308,807 B2 | 11/2012 | Seebeck et al. | |
| 8,350,186 B2 | 1/2013 | Jones et al. | |
| 8,414,648 B2 | 4/2013 | Reiley | |
| 8,430,930 B2 | 4/2013 | Hunt | |
| 8,454,705 B2 | 6/2013 | Pressacco et al. | |
| 8,475,503 B2* | 7/2013 | Denoziere | A61F 2/3094 |
| | | | 606/279 |
| 8,551,173 B2 | 10/2013 | Lechmann et al. | |
| 8,734,462 B2 | 5/2014 | Reiley et al. | |
| 8,796,015 B2 | 8/2014 | Gingras | |
| 8,828,311 B2* | 9/2014 | Medina | B23K 35/0244 |
| | | | 419/10 |
| 8,843,229 B2* | 9/2014 | Vanasse | A61F 2/30767 |
| | | | 700/98 |
| 8,864,826 B2 | 10/2014 | Pressacco | |
| 8,888,862 B2 | 11/2014 | McDonnell et al. | |
| 8,979,938 B2* | 3/2015 | Linares | A61F 2/38 |
| | | | 623/19.12 |
| 8,983,646 B1 | 3/2015 | Hanna | |
| 8,985,430 B2 | 3/2015 | Charlebois et al. | |
| 8,992,703 B2 | 3/2015 | O'Neill et al. | |
| 9,370,426 B2 | 6/2016 | Gabbrielli et al. | |
| 9,375,323 B2 | 6/2016 | Reiley | |
| 9,486,264 B2 | 11/2016 | Reiley et al. | |
| 9,801,974 B2 | 10/2017 | Landon | |
| 9,949,843 B2 | 4/2018 | Reiley et al. | |
| 10,045,854 B2 | 8/2018 | Adams | |
| 10,398,559 B2 | 9/2019 | Jones et al. | |
| 10,744,426 B2 | 8/2020 | Glover et al. | |
| 10,806,557 B1 | 10/2020 | Chen et al. | |
| 11,155,073 B2 | 10/2021 | O'Neill et al. | |
| 11,186,077 B2 | 11/2021 | O'Neill et al. | |
| 11,318,558 B2* | 5/2022 | O'Neill | B23K 26/064 |
| 11,351,021 B2* | 6/2022 | Patel | A61L 27/3629 |
| 11,510,783 B2 | 11/2022 | O'Neill et al. | |
| 11,517,438 B2* | 12/2022 | Tong | A61F 2/389 |
| 11,534,961 B2* | 12/2022 | Gold | B33Y 50/00 |
| 11,918,474 B2* | 3/2024 | Jones | B22F 10/38 |
| 2001/0014403 A1 | 8/2001 | Brown et al. | |
| 2002/0007294 A1 | 1/2002 | Bradbury et al. | |
| 2002/0010512 A1 | 1/2002 | Takei | |
| 2002/0015654 A1 | 2/2002 | Das et al. | |
| 2002/0016635 A1 | 2/2002 | Despres et al. | |
| 2002/0062154 A1 | 5/2002 | Ayers | |
| 2002/0102674 A1 | 8/2002 | Anderson | |
| 2002/0127328 A1 | 9/2002 | Shetty | |
| 2002/0128714 A1* | 9/2002 | Manasas | A61F 2/442 |
| | | | 623/17.15 |
| 2002/0130112 A1 | 9/2002 | Manasas et al. | |
| 2002/0138143 A1* | 9/2002 | Grooms | A61F 2/4644 |
| | | | 623/17.11 |
| 2002/0151983 A1 | 10/2002 | Shetty | |
| 2002/0173855 A1 | 11/2002 | Mansmann | |
| 2002/0187458 A1 | 12/2002 | Dolabdjian et al. | |
| 2002/0198528 A1 | 12/2002 | Engh et al. | |
| 2003/0012805 A1 | 1/2003 | Chen et al. | |
| 2003/0032351 A1 | 2/2003 | Horner et al. | |
| 2003/0033018 A1 | 2/2003 | Merchant | |
| 2003/0039676 A1* | 2/2003 | Boyce | A61F 2/32 |
| | | | 623/16.11 |
| 2003/0045941 A1 | 3/2003 | Lewallen | |
| 2003/0055500 A1 | 3/2003 | Fell et al. | |
| 2003/0055501 A1 | 3/2003 | Fell et al. | |
| 2003/0060882 A1 | 3/2003 | Fell et al. | |
| 2003/0060883 A1 | 3/2003 | Fell et al. | |
| 2003/0060884 A1 | 3/2003 | Fell et al. | |
| 2003/0060885 A1 | 3/2003 | Fell et al. | |
| 2003/0060888 A1 | 3/2003 | Fell et al. | |
| 2003/0065400 A1 | 4/2003 | Beam et al. | |
| 2003/0069638 A1 | 4/2003 | Barlow et al. | |
| 2003/0069718 A1 | 4/2003 | Hollister et al. | |
| 2003/0153977 A1 | 8/2003 | Suguro et al. | |
| 2003/0153981 A1* | 8/2003 | Wang | B22F 3/114 |
| | | | 623/22.21 |
| 2003/0155686 A1 | 8/2003 | Hawkins et al. | |
| 2003/0158606 A1 | 8/2003 | Coon et al. | |
| 2003/0180171 A1* | 9/2003 | Artz | C04B 38/067 |
| | | | 419/2 |

(56) References Cited

U.S. PATENT DOCUMENTS

| | | |
|---|---|---|
| 2003/0206820 A1 | 11/2003 | Keicher et al. |
| 2003/0209305 A1 | 11/2003 | Smith et al. |
| 2003/0220696 A1 | 11/2003 | Levine et al. |
| 2004/0006393 A1 | 1/2004 | Burkinshaw |
| 2004/0009228 A1 | 1/2004 | Tormala et al. |
| 2004/0015170 A1 | 1/2004 | Tallarida et al. |
| 2004/0023586 A1 | 2/2004 | Tilton |
| 2004/0044414 A1 | 3/2004 | Nowakowski |
| 2004/0054416 A1 | 3/2004 | Wyss et al. |
| 2004/0059356 A1 | 3/2004 | Gingras |
| 2004/0098132 A1 | 5/2004 | Andriacchi et al. |
| 2004/0121110 A1 | 6/2004 | Schmidt et al. |
| 2004/0143339 A1 | 7/2004 | Axelson et al. |
| 2004/0143341 A1 | 7/2004 | McLean |
| 2004/0148030 A1 | 7/2004 | Ek |
| 2004/0153163 A1 | 8/2004 | Posner |
| 2004/0162622 A1 | 8/2004 | Simon et al. |
| 2004/0167633 A1 | 8/2004 | Wen et al. |
| 2004/0191106 A1* | 9/2004 | O'Neill ............... B22F 10/80 419/2 |
| 2004/0199249 A1 | 10/2004 | Fell |
| 2004/0199250 A1 | 10/2004 | Fell |
| 2004/0204766 A1 | 10/2004 | Siebel |
| 2004/0230315 A1 | 11/2004 | Ek |
| 2004/0243237 A1 | 12/2004 | Unwin et al. |
| 2004/0267363 A1 | 12/2004 | Fell et al. |
| 2005/0033424 A1 | 2/2005 | Fell |
| 2005/0043816 A1 | 2/2005 | Datta et al. |
| 2005/0048193 A1 | 3/2005 | Li et al. |
| 2005/0049715 A1* | 3/2005 | Ito ............... A61L 27/12 435/395 |
| 2005/0070989 A1 | 3/2005 | Lye et al. |
| 2005/0079200 A1 | 4/2005 | Rathenow et al. |
| 2005/0085918 A1 | 4/2005 | Soffiati et al. |
| 2005/0085922 A1 | 4/2005 | Shappley et al. |
| 2005/0100578 A1* | 5/2005 | Schmid ............... A61L 27/56 623/16.11 |
| 2005/0103765 A1 | 5/2005 | Kawasaki |
| 2005/0112397 A1 | 5/2005 | Rolfe et al. |
| 2005/0123672 A1 | 6/2005 | Justin et al. |
| 2005/0154471 A1 | 7/2005 | Aram et al. |
| 2005/0169893 A1 | 8/2005 | Koblish et al. |
| 2005/0170159 A1 | 8/2005 | Ramsey et al. |
| 2005/0171604 A1 | 8/2005 | Michalow |
| 2005/0177169 A1 | 8/2005 | Fisher et al. |
| 2005/0192672 A1 | 9/2005 | Wyss et al. |
| 2005/0203630 A1 | 9/2005 | Pope et al. |
| 2006/0003179 A1* | 1/2006 | Wang ............... A61F 2/30767 427/2.26 |
| 2006/0015187 A1 | 1/2006 | Hunter et al. |
| 2006/0036251 A1 | 2/2006 | Reiley |
| 2006/0036331 A1 | 2/2006 | Lu et al. |
| 2006/0045903 A1 | 3/2006 | Kadiyala et al. |
| 2006/0058888 A1* | 3/2006 | Hunter ............... A61L 27/306 205/333 |
| 2006/0106419 A1 | 5/2006 | Gingras |
| 2006/0116774 A1 | 6/2006 | Jones et al. |
| 2006/0147332 A1* | 7/2006 | Jones ............... A61F 2/3094 148/513 |
| 2006/0241776 A1 | 10/2006 | Brown et al. |
| 2006/0241781 A1 | 10/2006 | Brown et al. |
| 2006/0254200 A1 | 11/2006 | Clarke et al. |
| 2007/0071733 A1 | 3/2007 | Kandel et al. |
| 2007/0135528 A1* | 6/2007 | Butler ............... C08J 9/28 521/61 |
| 2007/0142914 A1* | 6/2007 | Jones ............... B29C 37/0082 623/14.13 |
| 2007/0150068 A1* | 6/2007 | Dong ............... C23C 28/00 623/22.32 |
| 2007/0156249 A1 | 7/2007 | Lawrynowicz et al. |
| 2007/0158446 A1* | 7/2007 | Wang ............... A61L 27/30 239/11 |
| 2007/0173948 A1 | 7/2007 | Meridew et al. |
| 2007/0203584 A1 | 8/2007 | Bandyopadhyay et al. |
| 2007/0225390 A1 | 9/2007 | Wang et al. |
| 2008/0004709 A1 | 1/2008 | O'Neill et al. |
| 2008/0013170 A1* | 1/2008 | Tanaka ............... B23K 26/064 359/434 |
| 2008/0050412 A1 | 2/2008 | Jones et al. |
| 2008/0071381 A1 | 3/2008 | Buscher et al. |
| 2008/0161927 A1 | 7/2008 | Savage et al. |
| 2008/0206862 A1 | 8/2008 | Asgari |
| 2008/0288083 A1* | 11/2008 | Axelsson ............... A61F 2/30907 623/23.51 |
| 2009/0037148 A1* | 2/2009 | Lin ............... A61L 31/148 703/1 |
| 2009/0068245 A1 | 3/2009 | Noble et al. |
| 2009/0087605 A1 | 4/2009 | Ramsey et al. |
| 2009/0105772 A1 | 4/2009 | Seebeck et al. |
| 2009/0112315 A1 | 4/2009 | Fang et al. |
| 2009/0326671 A1* | 12/2009 | Schofield ............... B23K 26/355 606/1 |
| 2010/0010638 A1* | 1/2010 | Jones ............... A61L 27/306 623/23.12 |
| 2010/0057211 A1 | 3/2010 | Cuckler et al. |
| 2010/0137990 A1 | 6/2010 | Apatsidis et al. |
| 2010/0161061 A1* | 6/2010 | Hunt ............... A61B 17/1604 623/16.11 |
| 2010/0168856 A1* | 7/2010 | Long ............... A61F 2/30756 623/14.12 |
| 2010/0174377 A1 | 7/2010 | Heuer |
| 2010/0256758 A1 | 10/2010 | Gordon et al. |
| 2010/0268337 A1 | 10/2010 | Gordon et al. |
| 2010/0298950 A1 | 11/2010 | McDonnell et al. |
| 2011/0014081 A1* | 1/2011 | Jones ............... C23C 24/10 419/2 |
| 2011/0076316 A1 | 3/2011 | Sivananthan et al. |
| 2011/0200478 A1* | 8/2011 | Billiet ............... B22F 3/1125 264/414 |
| 2011/0245930 A1 | 10/2011 | Alley et al. |
| 2011/0257753 A1* | 10/2011 | Gordon ............... A61F 2/32 623/18.11 |
| 2011/0313532 A1 | 12/2011 | Hunt |
| 2012/0022662 A1 | 1/2012 | Conway et al. |
| 2012/0067853 A1* | 3/2012 | Wang ............... B23K 26/34 228/115 |
| 2012/0148987 A1 | 6/2012 | Dolabdjian et al. |
| 2012/0215310 A1 | 8/2012 | Sharp et al. |
| 2012/0245697 A1 | 9/2012 | Hunter et al. |
| 2012/0253474 A1 | 10/2012 | Klein et al. |
| 2013/0018483 A1* | 1/2013 | Li ............... B22F 3/105 427/2.24 |
| 2013/0030529 A1 | 1/2013 | Hunt |
| 2013/0056912 A1 | 3/2013 | O'Neill et al. |
| 2013/0123935 A1 | 5/2013 | Hunt et al. |
| 2013/0158672 A1 | 6/2013 | Hunt |
| 2013/0199748 A1* | 8/2013 | Christensen ............... B29C 64/153 164/494 |
| 2013/0218282 A1 | 8/2013 | Hunt |
| 2013/0268085 A1 | 10/2013 | Dong et al. |
| 2014/0058526 A1 | 2/2014 | Meridew et al. |
| 2014/0121776 A1 | 5/2014 | Hunt |
| 2014/0228969 A1 | 8/2014 | Engstrand et al. |
| 2014/0262006 A1 | 9/2014 | Biris |
| 2014/0277548 A1 | 9/2014 | Cohen et al. |
| 2014/0288649 A1 | 9/2014 | Hunt |
| 2014/0288650 A1 | 9/2014 | Hunt |
| 2014/0343681 A1 | 11/2014 | Cohen et al. |
| 2015/0045903 A1* | 2/2015 | Neal ............... B22F 5/106 219/76.14 |
| 2015/0258735 A1 | 9/2015 | O'Neill et al. |
| 2015/0374882 A1 | 12/2015 | McDemus et al. |
| 2017/0095337 A1 | 4/2017 | Pasini et al. |
| 2018/0055641 A1* | 3/2018 | Jones ............... B22F 10/38 |
| 2018/0055643 A1 | 3/2018 | Castro et al. |
| 2018/0228613 A1 | 8/2018 | Jones et al. |
| 2018/0280140 A1 | 10/2018 | Jones et al. |
| 2018/0280145 A1 | 10/2018 | Jones et al. |
| 2018/0361510 A1* | 12/2018 | Stamp ............... B29C 64/10 |
| 2019/0133770 A1 | 5/2019 | Dion et al. |
| 2019/0290441 A1* | 9/2019 | Tong ............... A61F 2/30771 |
| 2020/0086625 A1* | 3/2020 | O'Neill ............... B33Y 80/00 |

(56) References Cited

U.S. PATENT DOCUMENTS

| | | | |
|---|---|---|---|
| 2020/0179570 A1 | 6/2020 | Heschel et al. | |
| 2020/0281724 A1 | 9/2020 | Weber | |
| 2020/0315662 A1 | 10/2020 | Adam et al. | |
| 2020/0330235 A1 | 10/2020 | Bauer et al. | |
| 2021/0106426 A1 | 4/2021 | Zhang et al. | |
| 2021/0162731 A1 | 6/2021 | O'Neill et al. | |
| 2021/0282930 A1* | 9/2021 | Shi | A61F 2/28 |
| 2022/0117753 A1 | 4/2022 | Rucker et al. | |
| 2022/0142783 A1* | 5/2022 | Ahmadi | A61F 2/44 |

FOREIGN PATENT DOCUMENTS

| | | |
|---|---|---|
| CN | 101301230 A | 11/2008 |
| CN | 102087676 A | 6/2011 |
| DE | 19502733 A1 | 3/1996 |
| EP | 0 178 650 A2 | 4/1986 |
| EP | 0295038 A2 | 12/1988 |
| EP | 0 528 800 A1 | 3/1993 |
| EP | 0761242 A1 | 3/1997 |
| EP | 1247537 A1 | 10/2002 |
| EP | 1 300 511 A2 | 4/2003 |
| EP | 1418013 A1 | 5/2004 |
| EP | 1426013 A1 | 6/2004 |
| EP | 1455666 A1 | 9/2004 |
| EP | 1493455 A2 | 1/2005 |
| EP | 1683593 A2 | 7/2006 |
| EP | 1800700 A2 | 6/2007 |
| EP | 1806154 A1 | 7/2007 |
| EP | 1949989 A1 | 7/2008 |
| JP | H2255329 A | 10/1990 |
| JP | 4041794 A | 2/1992 |
| JP | H11287020 A | 10/1999 |
| JP | 11348045 A | 12/1999 |
| JP | 2001303751 A | 10/2001 |
| JP | 2003293012 A | 10/2003 |
| JP | 2006158953 A | 6/2006 |
| RU | 2218422 C2 | 12/2003 |
| WO | 9606881 A2 | 3/1996 |
| WO | 9824574 A1 | 6/1998 |
| WO | 9933641 A1 | 7/1999 |
| WO | 02085246 A2 | 10/2002 |
| WO | 2005/084216 A2 | 9/2005 |
| WO | 2005080029 A1 | 9/2005 |
| WO | 2005087982 A1 | 9/2005 |
| WO | 2007058160 A1 | 5/2007 |
| WO | 2009116950 A1 | 9/2009 |
| WO | 2011002765 A2 | 1/2011 |
| WO | 2013006778 A2 | 1/2013 |

OTHER PUBLICATIONS

Created and Designed by Shaman Gaspar, Maintained by Peter Fox, "Direct Laser Remelting", "Project Web Site", Using Lasers to Grow 3D object on Stainless Steel; The University of Liverpool 2002; http://mserc.liv.ac.uk/research/dlr/dlr_html.
Vureal et al., Plasma-sprayed oxide ceramics on steel substrates, Surface Coatings and Technology, 97 (1997) 347-354.
Patello-femoral Arthroplasty X-ray Results, Stryker Howmedica Osteonics, published on or before Apr. 5, 2011.
The Metals Handbook, Desk Edition, 2nd Edition, ASM International, 1998, p. 29.
Hawley's Condensed Chemical Dictionary, 14th edition. John Wiley & Sons, 2002. Definition: sintering.
Dr. Kerron Harvey, producer, Research Intelligence, The University of Liverpool, Issue 13, Jun. 2002.
H.J. Niu and I.T.H. Chang, "Selective Laser Sintering of Gas and Water Atomized High Speed Steel Powders," Scripta Materialia vol. 41, No. 1, (1999), pp. 25-30.
Meiners et al., "Direct Generation of Metal Parts and Tools by Selective Laser Powder Remelting (SLPR)", W. Meiners, C. Over, K. Wissenbach, R. Poprawe, pp. 655-661 Austin, Texas, Aug. 9-11, 1999.
European Search Report and Written Opinion, EP05028133, dated May 11, 2010.
European Search Report and Written Opinion, EP10162970, dated Jun. 17, 2010.
R. Morgan, C.J. Sutcliffe, W. O'Neill, "Experimental investigatoin of nanosecond pulsed Nd:YAG laser re-melted pre-placed powder beds," Rapid Prototyping Journal, vol. 7, No. 3, 2001, pp. 159-172.
N.K. Vail, L.D. Swain, W.C. fox, T.B. Aufdlemorte, G. Lee, J.W. Barlow, "Materials for biomedical applications," Materials and Design, 20, 1999, pp. 123-132.
R.H. Morgan, A.J. Papworth, C. Sutcliffe, P. Fox, W. O'Neill, "High density net shape components by direct laser re-melting of single phase powders," Journal of Materials Science, 37, 2002, pp. 3093-3100.
European Search Report and Written Opinion, EP06127218, dated May 6, 2010.
PCT/US2008/008955 International Search Report and Written Opinion mailed Dec. 2, 2008.
PCT/US2008/008955 International Preliminary Report on Patentability mailed Feb. 4, 2010.
Chua, C.K. et al., Development of a Tissue Engineering Scaffold Structure Library for Rapid Prototyping. Parts 1 and 2, International Journal of Advanced Manufacturing Technology, Feb. 2003, vol. 21, pp. 291-312.
Bobyn et al., "The optimum pore size for the fixation of porous-surfaced metal implants by the ingrowth of bone", Clinical Orthopaedics and Related Research, 150; 263-270 (1980).
Notice of Opposition for EP Application No. 06125422.3 dated Jul. 4, 2011.
Protek Cementless Replacement of the Acetabulum by E. Morscher, published on or before Apr. 5, 2011.
Interlocutory Decision for Application No. EP 06125422.3 dated Nov. 14, 2012.
European Examination Report for Application No. EP10162970.7 dated Dec. 3, 2013.
"Solid Freeform Fabrication", IEEE Spectrum, Feb. 1999, pp. 34-43.
Custom Design and Manufacturing of Canine Knee Implants, <http://www.lib.ncsu.edu/resolver/1840.16/670>, Issued Dec. 2, 2003.
European Examination Report for Application No. EP10162970.7 dated Aug. 4, 2017.
Cheah et al., Automatic Algorithm for Generating Complex Polyhedral Scaffold Structures for Tissue Engineering, Tissue Engineering, vol. 10, No. 3/4, pp. 595-610, Mar. 2004.
Heinl et al., Cellular Ti—6Al—4V structures with interconnected macro porosity for bone implants fabricated by selective electron beam melting, Acta Biomaterialia, vol. 4, Issue 5, pp. 1536-1544, Sep. 2008.
Tuan et al., "Application of Micro CT and Computation Modeling in Bone Tissue Engineering", Computer-Aided Design, vol. 37, No. 11, Sep. 2005, pp. 1151-1161.
Wang et al., "A Hybrid Geometric Modeling Method for Large Scale Conformal Cellular Structures," ASME Design Engineering Technical Conferences, Sep. 2005, 7 pages.
Akamaru et al., "Healing of Autologous Bone in a Titanium Mesh Case Used in Anterior Column Reconstruction After Total Spondylectomy", SPINE vol. 27, No. 13, 2002, pp. E329-E333.
Mcafee et al., "Current Concepts Review: Interbody Fusion Cages in Reconstructive Operations on the Spine", The Journal of Bone and Joint Surgery, vol. 81, Issue 6, Jun. 1999, pp. 859-880.
Lin et al., "Interbody Fusion Cage Design Using Integrated Global Layout and Local Microstructure Topology Optimization", SPINE vol. 29, No. 16, pp. 1747-1754, Aug. 2004.
Williams et al., "CT evaluation of lumbar interbody fusion: Current concepts", AJNR Am J Neuroradiol 26:2057-2066, Sep. 2005.
EBI Learning Center Cafe flyer, EBI Spine EBI & Interpore Cross, NASS Booth 801, prior to Sep. 27, 2005, Philadelphia, PA.
Stephen D. Kuslich, MD, "Lumbar Interbody Cage Fusion for Back Pain: An Update on the Bak (Bagby and Kuslich) System", SPINE: State of the art reviews—vol. 13, No. 2, May 1999, pp. 295-311.
Zdeblick et al., "LT-CAGE—Lumbar Tapered Fusion Device— Surgical Technique", Medtronic Sofamor Danek, 25 pages, Copyright 2000.

(56) References Cited

OTHER PUBLICATIONS

Cheung et al., "Spinal Instrumentation Overview in Lumbar Degenerative Disorders: Cages", Chapter 26 / Spinal-Instrumentation Overview, Section IV/Surgery, Lumbar Spine: Official Publication of the International Society for the Study of the Lumbar Spine (3), 2004, pp. 286-291.
Kim et al., "Spinal Instrumentation Surgical Techniques", Thieme Medical Publishers, Inc., New York, NY, Copyright 2005, 41 pages.
Lin et al., "Structural and mechanical evaluations of a topology optimized titanium interbody fusion cage fabricated by selective laser melting process", revised Aug. 25, 2006, accepted Dec. 2006, Published online Apr. 5, 2007 in Wiley Interscience (www.interscience.wiley.com). DOI: 10.1002/jbm.a.31231. 8 pages.
Third Party Observation for EP05028133.6 dated Mar. 25, 2019, 3 pages.
Third Party Observation for EP05028133.6 dated May 18, 2020, 3 pages.
Williams, et al., "Advances in Modeling the Effects of Selected Parameters on the SLS Process," Rapid Prototyping Journal, Jun. 1, 1998, pp. 90-100, vol. 4, No. 2.
Filiz et al., Int. Journal of Machine Tools & Manufacture, 48, 459-472, 2008.
Canadian Office Action for Application No. 2,529,884 dated Mar. 27, 2013.
Australian Examination Report for Application No. 2013202686 date Aug. 7, 2014.
Chen, "3D Texture Mapping for Rapid Manufacturing", Computer-Aided Design and Applications, University of Southern California, vol. 4, No. 6, pp. 761-771, Jan. 1, 2007.
Engelbrecht et al., Cellular Structures for Optimal Performance, Georgia Institute of Technology & Paramount Industries, Inc., 2009.
Wang, Computer-Aided Design Methods for Additive Fabrication of Truss Structures, Georgia Institute of Technology, 2002.
Australian Examination Report for Application No. 2013202075 dated Feb. 13, 2015.
Canadian Office Action and Examination Search Report for Appln. No. 2,860, 188 dated Jun. 4, 2015.
European Examination Report for Application No. 10162970.7 dated Feb. 9, 2016.
Cunningham et al., "Design of Interbody Fusion Cages: Historical Considerations and Current Perspectives in Cage Technology", Surgical Techniques; Spinal Implants; Chapter 29-31, 2006, pp. 421-465.
Inter Fix Threaded Fusion Device, Important Medical Information, 14 pages.

* cited by examiner

FIG. 7

| METAL POWDER | MEAM OVERLAP (%) | -500 | | | | | | | | | -250 | | | | | | | |
|---|---|---|---|---|---|---|---|---|---|---|---|---|---|---|---|---|---|---|
| | LASER SCANNING SPEED (mm/s) | 100 | 120 | 140 | 160 | 180 | 200 | 220 | 240 | 260 | 100 | 120 | 140 | 160 | 180 | 200 | 220 | 240 |
| | SUBSTRATE | | | | | | | | | | | | | | | | | |
| CoCr | Ti ALLOY | | | | | | | | | | | | | | | | | |
| | CoCr | | | | | | | | | | | | | | | | | |
| | STAINLESS STEEL | ✓ | ✓ | ✓ | ✓ | ✓ | ✓ | ✓ | ✓ | ✓ | ✓ | ✓ | ✓ | ✓ | ✓ | ✓ | ✓ | |
| Nb | Ti ALLOY | | | | | | | | | | | | | | | | | |
| | CoCr | | | | | | | | | | | | | | | | | |
| | STAINLESS STEEL | | | | | | | | | | | | | | | | | |
| Ta | Ti ALLOY | | | | | | | | | | | | | | | | | |
| | CoCr | | | | | | | | | | | | | | | | | |
| Ti | Ti ALLOY | | | | | | | | | | | | | | | | | |
| | CoCr | | | | | | | | | | | | | | | | | |

| 0 | MEAM OVERLAP (%) | -40 | | | | | | | | | 25 | | | | | | | |
|---|---|---|---|---|---|---|---|---|---|---|---|---|---|---|---|---|---|---|
| | LASER SCANNING SPEED (mm/s) | 160 | 170 | 180 | 190 | 200 | 210 | 220 | 230 | 240 | 100 | 120 | 140 | 160 | 180 | 200 | 220 | 240 |
| | SUBSTRATE | | | | | | | | | | | | | | | | | |
| CoCr | Ti ALLOY | | | | | | | | | | ✓ | ✓ | ✓ | ✓ | ✓ | ✓ | ✓ | |
| | CoCr | | | | | | | | | | ✓ | ✓ | ✓ | ✓ | ✓ | ✓ | ✓ | |
| | STAINLESS STEEL | | | | | | | | | | ✓ | ✓ | ✓ | ✓ | ✓ | ✓ | ✓ | |
| Nb | Ti ALLOY | ✓ | ✓ | ✓ | ✓ | ✓ | ✓ | ✓ | ✓ | | | | | | | | | |
| | CoCr | ✓ | ✓ | ✓ | ✓ | ✓ | ✓ | ✓ | ✓ | ✓ | | | | | | | | |
| | STAINLESS STEEL | ✓ | ✓ | ✓ | ✓ | ✓ | ✓ | ✓ | ✓ | | | | | | | | | |
| Ta | Ti ALLOY | ✓ | ✓ | ✓ | ✓ | ✓ | ✓ | ✓ | ✓ | | | | | | | | | |
| | CoCr | ✓ | ✓ | ✓ | ✓ | ✓ | ✓ | ✓ | ✓ | | | | | | | | | |
| Ti | Ti ALLOY | ✓ | ✓ | ✓ | ✓ | ✓ | ✓ | ✓ | ✓ | | | | | | | | | |
| | CoCr | ✓ | ✓ | ✓ | ✓ | ✓ | ✓ | ✓ | ✓ | ✓ | | | | | | | | |

| 0 | MEAM OVERLAP (%) | 50 | | | | | | | | | 50 | | | | | | | |
|---|---|---|---|---|---|---|---|---|---|---|---|---|---|---|---|---|---|---|
| | LASER SCANNING SPEED (mm/s) | 100 | 120 | 140 | 160 | 180 | 200 | 220 | 240 | 260 | 280 | 300 | 320 | 340 | 360 | 380 | 400 | 420 |
| | SUBSTRATE | | | | | | | | | | | | | | | | | |
| CoCr | Ti ALLOY | | | | | | | | | | | | | | | | | |
| | CoCr | | | | | | | | | | | | | | | | | |
| | STAINLESS STEEL | ✓ | ✓ | ✓ | ✓ | ✓ | ✓ | ✓ | ✓ | ✓ | ✓ | ✓ | ✓ | ✓ | ✓ | ✓ | ✓ | |
| Nb | Ti ALLOY | | | | | | | | | | | | | | | | | |
| | CoCr | | | | | | | | | | | | | | | | | |
| | STAINLESS STEEL | ✓ | ✓ | ✓ | ✓ | ✓ | ✓ | ✓ | ✓ | ✓ | | | | | | | | |
| Ta | Ti ALLOY | | | | | | | | | | | | | | | | | |
| | CoCr | | | | | | | | | | | | | | | | | |
| Ti | Ti ALLOY | | | | | | | | | | | | | | | | | |
| | CoCr | | | | | | | | | | | | | | | | | |

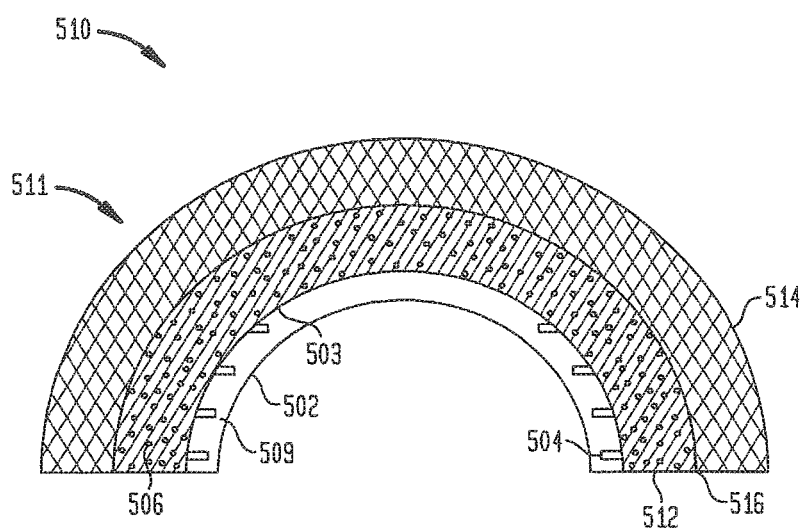

LASER-PRODUCED POROUS SURFACE

CROSS-REFERENCE TO RELATED APPLICATION

The present application is a continuation of U.S. patent application Ser. No. 18/411,633, filed on Jan. 12, 2024 which is a continuation of U.S. patent application Ser. No. 16/900,219, filed Jun. 12, 2020 which is a continuation of U.S. patent application Ser. No. 15/788,304 filed Oct. 19, 2017, which is a continuation of U.S. patent application Ser. No. 14/276,483 filed May 13, 2014, now U.S. Pat. No. 10,398,559, which is a continuation of U.S. patent application Ser. No. 11/295,008 filed Dec. 6, 2005, now U.S. Pat. No. 8,728,387, the disclosures of which are hereby incorporated herein by reference.

BACKGROUND OF THE INVENTION

The present invention relates to a device having a porous surface attached directly or indirectly to a bearing surface and a method for forming the same.

In particular, this invention relates to a computer-aided laser apparatus or other suited high energy beam, which sequentially remelts a plurality of powder layers to build a porous layer in a layer-by-layer fashion.

The present invention also includes a method of attaching or connecting a bearing surface directly or indirectly preferably formed from a polymer to the sequentially-built porous part.

The present application is particularly directed toward a method of forming a porous and partially-porous metallic structure having a bearing surface.

The field of free-form fabrication has seen many important recent advances in the fabrication of articles directly from computer-controlled databases. These advances, many of which are in the field of rapid prototyping of articles such as prototype parts and mold dies, have greatly reduced the time and expense required to fabricate articles, particularly in contrast to conventional machining processes in which a block of material, such as a metal, is machined according to the engineering drawings. One example of a modern rapid prototyping technology is the selective laser sintering process practiced by systems available from 3D Systems, Valencia, California. According to this technology, articles are produced in a layer-wise fashion, from a laser-fusible powder that is dispensed one layer at a time. The powder is fused, remelted or sintered, by the application of laser energy that is directed in raster-scan fashion to portions of the powder layer corresponding to a cross-section of the article. After fusing of the powder on one particular layer, an additional layer of powder is dispensed, and the process repeated with fusion taking place between the current layer and the previously laid layers, until the article is complete.

The field of rapid prototyping of parts has, in recent years, made large improvements in broadening high strain, high density parts for use in the design and pilot production of many useful articles including metal parts. These advances have permitted the selective laser remelting and sintering process to now also be used in fabricating prototype tooling for injection molding, with expected tool life in excess of 10,000 mold cycles. The technologies have also been applied to the direct fabrication of articles, such as molds from metal powders without a binder. Examples of metal powder reportedly used in such direct fabrication include two-phase metal powders of the copper-tins, copper-solder (the solder being 70% lead and 30% tin), and bronze-nickel systems. The metal articles formed in these ways have been quite dense, for example, having densities of up to 70% to 80% of full density (prior to any infiltration). Prior applications of this technology have strived to increase the density of the metal structure formed by the melting or sintering process. The field of rapid prototyping of parts has focused on providing high strength, high density parts for use and design in production of many useful articles, including metal parts.

But while the field of rapid prototyping has focused on increasing density of such three-dimensional structures, the field has not focused its attention on reducing the density of three-dimensional structures. Consequently, applications where porous and partially-porous metallic structures, and more particularly metal porous structures with interconnective porosity, are advantageous for use, have been largely ignored.

In addition, many structures, especially in the medical arts, require two different surfaces, each adapted for their own purposes. Along this line, a structure may have a first surface which needs to be porous for tissue in-growth and a second surface which should be adapted to be a bearing surface. Further, the first surface or portion may include different layers having different gradients of porosity. For example, the first surface may include an outer region having a porosity of approximately 80%. As you move normal with regard to the first surface the porosity may alter such that the porosity is increased or in a preferred embodiment, the porosity decreases even until the porosity is almost zero. Of course, the present invention contemplates a situation where the porosity alters from position to position depending on the requirements of the device.

Although different techniques have tried to provide such a method and apparatus, still greater techniques are needed in this area.

SUMMARY OF THE INVENTION

In one embodiment, the present invention relates to a method of forming an implant having a porous tissue ingrowth structure and a bearing support structure. The method may include depositing a first layer of a metal powder onto a substrate. Next, a laser beam scans over the powder so as to sinter the metal powder at predetermined locations. At least one layer of the metal powder may be deposited onto said first layer while repeating the laser scanning step for each successive layer until a predetermined structure having a first surface and a second surface is constructed. A flowable polymer is placed into contact with the second surface of said predetermined structure. The polymer is cooled such that the flowable polymer adheres to the second surface of the structure. The laser scanning step may include scanning the laser beam onto the metal powder to form a portion of a plurality of predetermined unit cells within the metal powder.

The method may include placing the predetermined structure into a cavity of a die and depositing a polymer onto the second surface of the predetermined structure within the cavity of the die. The step of placing a flowable polymer in contact with the second surface of the predetermined structure may include applying pressure and heat to the polymer in the cavity of the die. The step of placing the flowable polymer in contact with the second surface of the predetermined structure may include transferring the flowable polymer onto the second surface. The step of placing the flowable polymer in contact with the second surface of the predetermined structure may include placing the second surface of the predetermined structure adjacent a polymer structure, applying heat to the polymer structure and allowing the polymer structure to engage the predetermined structure. The predetermined structure may include an outer layer, an intermediate layer and an inner layer, the outer layer and the inner layer being relatively porous and the intermediate layer being relatively dense such that the flowable polymer cannot substantially leech through the intermediate layer from the inner layer to the outer layer. The outer layer has a porosity approximately between 60% to 80% and the inner layer has a porosity approximately higher than 80%. The outer layer may have a pore size distribution in the range of 80 μm to 800 μm and the inner layer may have a pore size distribution higher than approximately 800 μm.

The predetermined structure may have a gradient porosity. The gradient porosity of the predetermined structure may include a first layer that is substantially porous, a second layer that is substantially non-porous, a third layer that is substantially porous such that the flowable polymer cannot substantially leech through the second layer from the third layer to the first layer when the flowable liquid polymer is placed in contact with the third layer.

The present invention also includes a medical implant including a metal insert having a bone ingrowth structure, an intermediate structure and a bearing support structure, the bone ingrowth structure having a porosity sufficient to promote bone ingrowth. The implant also includes a bearing surface formed from a polymer material, the bearing surface being attached to the bearing support structure. The intermediate structure has a porosity sufficient to inhibit the polymer material from translating through the bearing support structure to the bone ingrowth structure. The intermediate structure may be designed to facilitate a specific stiffness characteristic to an overall construct and/or include two barrier layers and a bridging section.

BRIEF DESCRIPTION OF THE DRAWINGS

FIG. 7 is a table showing a series of parameters used for making samples according to the present invention;

FIG. 24 is an illustration of an alternate embodiment of an acetabular cup.

DETAILED DESCRIPTION

The present invention relates to a method of forming a porous or partially porous metallic structure having a bearing surface attached directly or indirectly thereto. The structures are particularly but not exclusively applicable for use in the art of soft tissue interlock structures for medical implants and prosthesis.

The method makes use of laser technology or any other high energy beam by employing a variety of scanning strategies.

Typical metal and metal alloys employed include stainless steel, cobalt chromium alloys, titanium and its alloys, tantalum and niobium, all of which have been used in medical device applications. The present invention can be used for such medical device applications where bone and/or soft tissue interlock with the component is required, or where a controlled structure is required to more closely match mechanical properties of the device with surrounding tissue.

Additionally, the present invention may be employed to enhance the biocompatibility of a porous structure with human tissue while also providing a bearing surface that is resistant to wear. With these advantages in mind, a structure may be created using specific dimensions required to accommodate a particular patient.

The porous and partially porous metallic structures may be attached or incorporated to a surface, which will be used as a bearing surface, as is described below. By interconnecting or having an implant with a porous structure adjacent a bearing surface, the orthopedic implant can provide a structure for permitting bone and soft tissue interlock in combination with a bearing surface that enables the implant to rotate, articulate or pivot relative to an additional bearing surface.

Figure 1A:
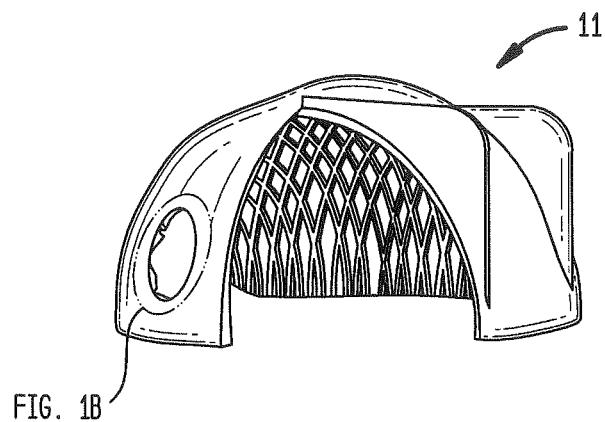
FIG. 1A is one embodiment of a metal insert of an acetabular cup constructed according to the present invention.
Figure 1B:
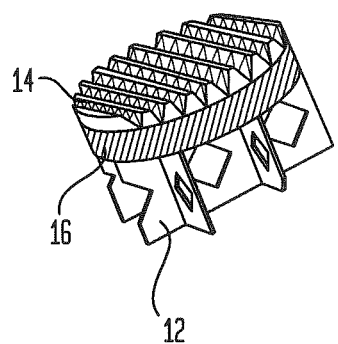
FIG. 1B illustrates a cut out portion of the metal insert of FIG. 1A.

As shown in FIGS. 1A and 1B, the device for implantation into the body may be in the form of an acetabular cup 10. The acetabular cup 10 preferably includes a metal insert 11 comprised of a bearing support structure 12, a bone ingrowth structure 14 and an intermediate structure 16. The acetabular cup 10 can be used in a total hip replacement surgery.

Figure 2:
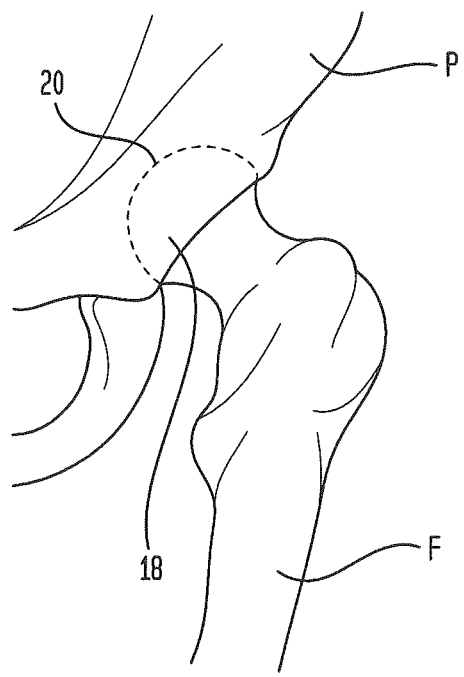
FIG. 2 is a schematic drawing of a pelvis region.
Figure 3:
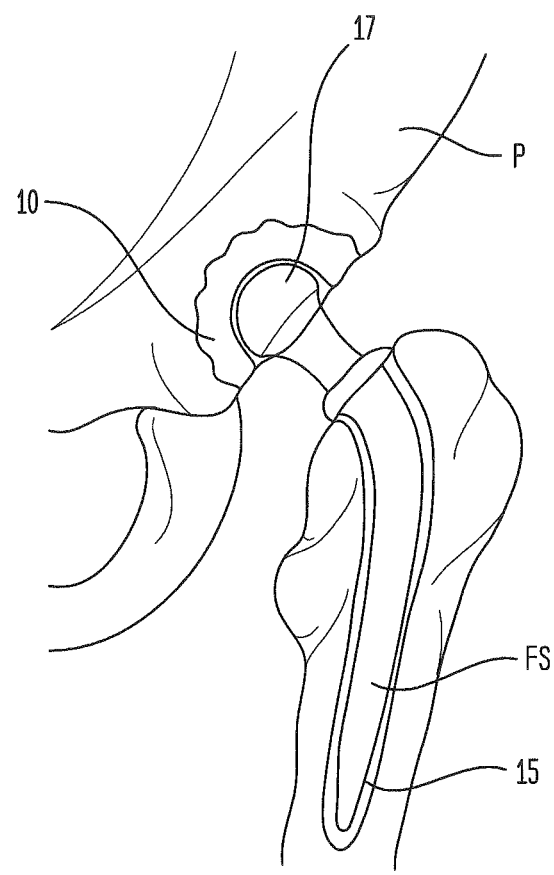
FIG. 3 is a schematic drawing of an acetabular cup and a femoral stem implanted into the pelvic region.

During the surgery, the joint of the hip, as shown in FIGS. 2 and 3, the hip socket 20 (acetabulum) and the ball 18 or head of the femur F are removed. An acetabular cup, such as acetabular cup 10, is positioned within the pelvis P. A first end 15 of a femoral stem FS is positioned within the femur F, while a second end 17, including a "ball" is positioned adjacent the bearing support structure 12 of the acetabular cup 10. Desirably, the second end 17 of the femoral stem FS is rotatably moveable relative to the acetabular cup 10.

The bone ingrowth structure 14, as well as the bearing support structure 12 and intermediate structure 16 of the acetabular cup 10 may be constructed using a direct laser remelt process as, for example, described in U.S. patent application Ser. No. 10/704,270, filed Nov. 7, 2003 entitled "Laser-Produced Porous Surface," and U.S. patent application Ser. No. 11/027,421, filed Dec. 30, 2004, entitled "Laser-Produced Porous Structure," the disclosures of which are hereby incorporated herein by reference.

As shown in FIG. 1A, in one preferred embodiment of the present invention, the bone ingrowth structure 14 is approximately 1.1 mm thick and has a porosity of approximately between the range of 70% to 80%. The intermediate structure 16 is approximately 0.1 mm thick and is substantially fully dense. The bearing support structure 12 is approximately 0.8 mm thick and is adapted for being secured within a polymer layer to form a bearing surface 8, as will be described below. The incorporation of the polymer, as described below, desirably results in an acetabular cup with a thickness of less than 4 mm, which is considered to be preferentially for resurfacing cups. The measurements are simply illustration and should not be considered a limitation since various thicknesses may be used when building the part.

Figure 1C:
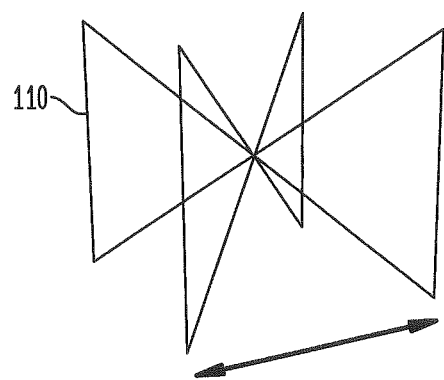
FIG. 1C is a unit cell used to construct a portion of the metal insert of FIG. 1A.
Figure 1D:
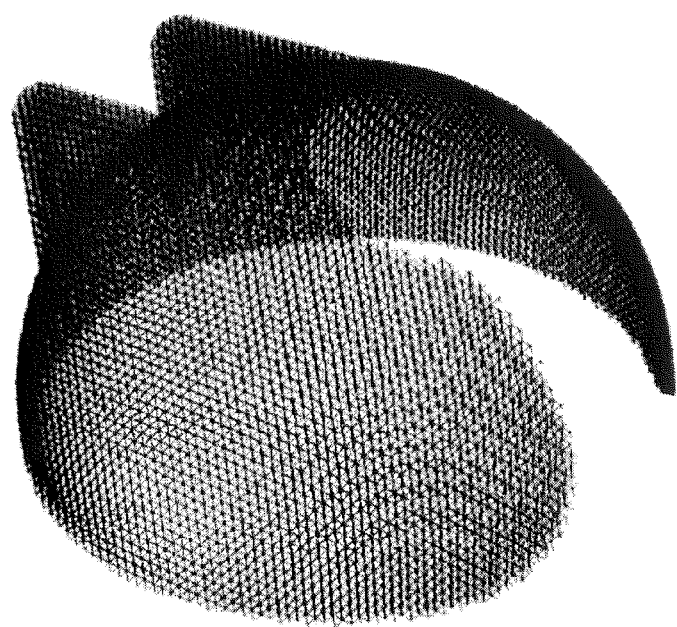
FIG. 1D is a computer model of a portion of an acetabular cup constructed using the unit cell of FIG. 1C.

The bone ingrowth structure 14 may be prepared by populating the volume of the structure with a single unit repeating cell using propriety software. A single unit cell 110 and the corresponding porous layer are shown in FIGS. 1C and 1D. The single cell 110 used is a unit cell octahedron structure having a length of 800 μm with vertical pillars on each corner. When tessellated, these cells produce porous structures having a porosity of approximately 80% with full interconnected porosity and mean pore sizes between 100 μm and 400 μm.

The intermediate structure 16 is designed to facilitate the bonding of the bearing support structure 12 to the bone ingrowth structure 12, as well as isolate the bone ingrowth structure from a polymeric material, as will be described below.

Figure 1E:
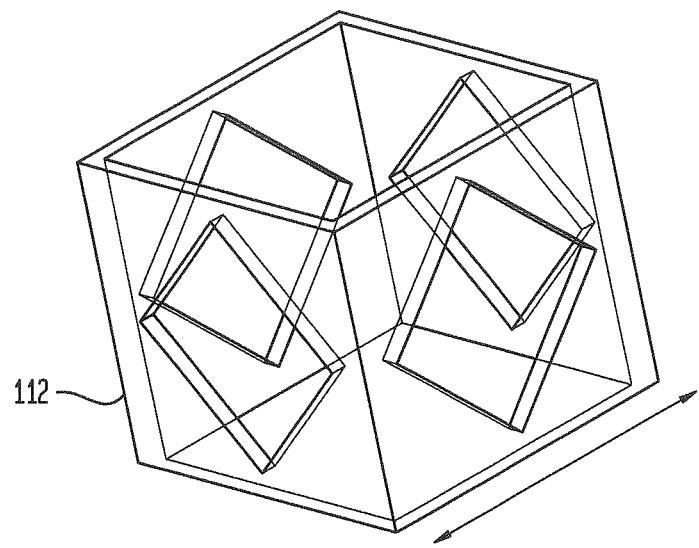
FIG. 1E is a unit cell used to construct a portion of the metal insert of FIG. 1A.
Figure 1F:
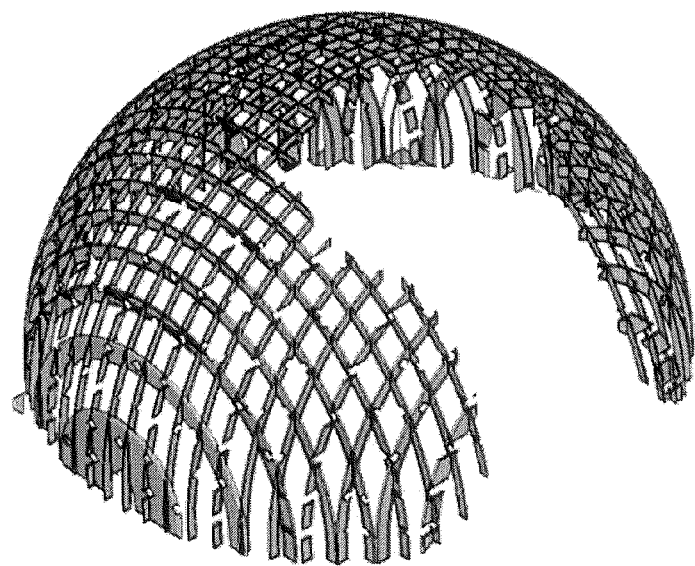
FIG. 1F is a computer model of a portion of an acetabular cup constructed using the unit cell of FIG. 1E.

The bearing support structure 12 may be designed by populating the volume of the structure with a single repeating unit cell 112, as shown in FIGS. 1E and 1F. This produces a structure that is between 90% to 95% porous with fully interconnected porosity with pore sizes between 1.25 mm and 2 mm diameter. Of course, the dimension of the unit cell 112 may be altered or even a difference unit cell employed, such that the porosity of the structure may be customized based on desirability.

The porosity of each structure may be altered but in a preferred embodiment the porosity of each structure is dependent on that structures function. Thus the resultant porosity of the bone ingrowth structure 14 should be within a range that promotes bone ingrowth. The porosity of the bearing support structure 12 should be in a range that easily allows for a polymeric material or other material to adhere to the structure as will be described below. And the porosity of the intermediate layer should be in a range that prohibits or at least reduces the ability of a polymeric material to leech from the bearing support structure 12 to the bone ingrowth structure 14, as will be described below.

Figure 1G:
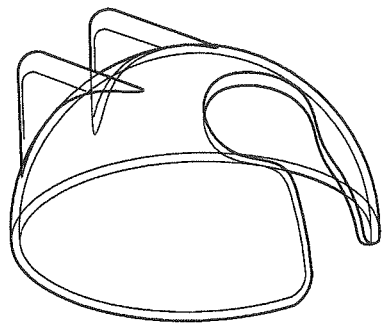
FIG. 1G is a computer rendering of an acetabular cup including the portions illustrated in FIGS. 1D and 1F.

The files describing the bone ingrowth structure 14, solid intermediate structure 16 and the bearing support structure 12 may all be loaded into the operating software for a MCP realizer, FUSCO. The three structures are then reassembled and manufactured as one part. A schematic of the manufactured part and a photo of the final component are shown in FIG. 1G.

In one specific embodiment, the acetabular cup has a total thickness of 3 mm and an internal diameter of 46 mm.

According to one method of forming a porous three-dimensional structure by laser melting, a powder of titanium, titanium alloys, stainless steel, cobalt chrome alloys, tantalum or niobium is disposed onto a substrate. The laser melting process includes scanning a laser beam onto the powder and in parallel scan lines with a beam overlap, e.g., scan spacing, followed by similar additional scans or subsequent scans at 90 degrees, as way of example. The type of scan chosen may depend on the initial layer thickness as well as the web height required. The web height refers to the height of a single stage of the metal structure 11. The web height may be increased by depositing additional layers of powder of a structure and scanning the laser at the same angle of the previous scan. Further, the additional scan lines may be at any angle to the first scan, to form a structure with the formation of a defined porosity, which may be regular or random. The scanned device may be programmed to proceed in a random generated manner to produce an irregular porous construct but with a defined level of porosity. Furthermore, the scan can be preprogrammed using digitized images of various structures, such as the acetabular cup 10, shown in FIGS. 1A and 1B, to produce a similar structure. The scan may also be customized to a particular patient. In this process, a CT scan of for instance, a person's acetabullum is taken and inputted into a computer program. The resultant file may be sliced, digitized or manipulated by methods known to those in the art as well as described herein. Based on these files and tailored measurements, a customized implant may be fabricated for a particular individual.

To produce a bone ingrowth structure, such as the bone ingrowth structure 14 of the acetabular cup 10, the nature of the material formed as a result of laser melting of powder beads is principally dependent upon the thermal profile involved (heating rate, soaking time, cooling rate); the condition of the raw material (size and size distribution of powder particles); atmospheric conditions (reducing, inert or oxidizing chamber gas); and accurate control of the deposited layer thickness.

The most optimum porous structure for maximization of bone in-growth on a prosthesis has generally been found to be between approximately 60% to 80%. The preferred pore structure is irregular and interconnected, with a minimum pore size between about 80 µm and 100 µm and a maximum pore size between 80 µm and 800 µm.

Figure 4:
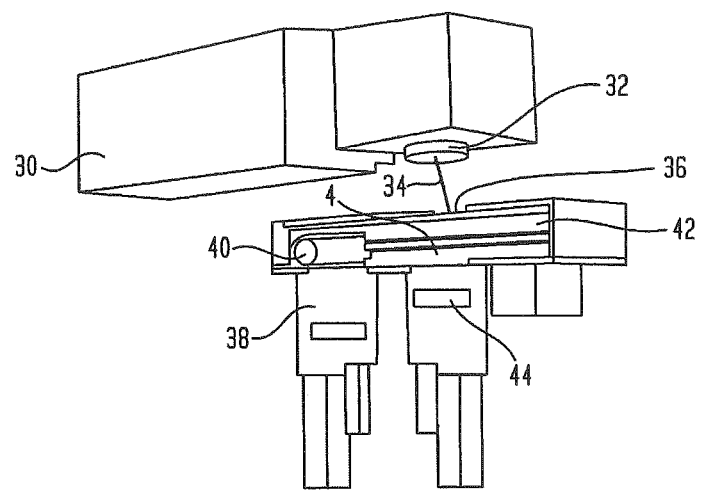
FIG. 4 is an illustration of an apparatus used in conjunction with the present invention.

The bone ingrowth structure 14, the bearing support structure 12 and the intermediate structure 16 of the acetabular cup 10 may be constructed using the apparatus shown in FIG. 4 of 5. The apparatus of FIG. 4 may include an Nd; YAG industrial laser 30, integrated to an RSG 1014 analog galvo-scanning head 32 for providing a maximum scan speed of 500 mm per second. The laser beam 34 is directed into an atmospherically-controlled chamber 36, which consists of two computer-controlled platforms with powder delivery and part building. The powder is delivered from a variable capacity chamber 38 into the chamber 36 and is transported by a roller 40 to a build platform 42 above a variable capacity build chamber 44.

Figure 6:
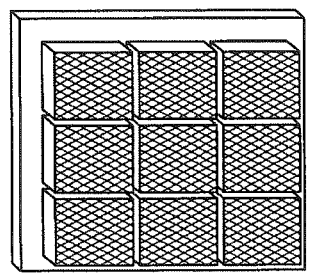
FIG. 6 is a sample of constructed coupons using a method according to the present invention.

In one embodiment as shown in FIG. 4, the build and delivery system parameters are optimized for an even 100 µm coating of powder to be deposited for every build layer. For implant manufacture, the metals chosen as surface materials are all difficult to process due to their affinity for oxygen. Titanium and other alloys are easily oxidized when processed by laser in oxygen-containing atmosphere, their oxide products have high melting points and poor flowability. For this reason, and to prevent the formation of other undesirable phases, the methods may be carried out under an Argon inert atmosphere in chamber 36. Pressure may remain at or below atmospheric pressure during the entire application. In another example of forming a porous structure, a cobalt chrome alloy may be configured into square structures, called coupons. As shown in FIG. 6, an array of cobalt chrome coupons may be built onto a stainless steel substrate. The coupons were built as test subjects. The cobalt chrome alloy may have a particle size distribution of 90 less than 22 µm, i.e., 90% of the particles are less than 22 µm, the composition of which is shown in the table below.

TABLE 1

Composition of Co212-e CoCr alloy

| Element | | | | | | | | |
|---|---|---|---|---|---|---|---|---|
| Cr | Mo | Si | Fe | Mn | Ni | N | C | Co |
| Wt % 27.1 | 5.9 | 0.84 | 0.55 | 0.21 | 0.20 | 0.16 | 0.050 | Balance |

An array of nine sample coupons were produced as shown in FIG. 6, with the process of Table 2, using a maximum laser power of 78 watts (W) and laser scanning speed for each coupon varying between 100-260 mms-1. Of course a higher laser power may be employed; however, a higher laser power would also necessitate increasing the speed of the laser scan speed in order to produce the desired melting of the powder layer. A simple linear x-direction scan was used on each of the coupons. This allowed the processing parameter, beam overlap, to be used to control the space between successive scan lines. That is, with a 100 µm laser spot size, an overlap of −200% produces a 100 µm gap between scans. Although the acceptable range for the beam overlap is given at +50% to −1200% it should be duly noted that the negative number only refers to the fact the there is a gap as opposed to a beam overlap between successive scans. For instance a beam overlap of zero refers to the fact that successive scans on the same layer of powder border each other. A positive beam overlap produces more solid components in contrast to a more negative beam overlap, which produces a more porous structure. The less the beam overlap the more solid the resultant structure will be. In addition, a larger beam overlap may be used to create the attachment structure or bearing support structure 12, as compared to the intermediate structure 16. If the beam overlap was 5%, then 5% of the first scan is overlapped by the second scan. When computing the Andrew number the absolute value of the beam overlap is used. The complete set of process parameters used is shown in Table 2 below.

TABLE 2

Process parameters

| Power Watts (W) | Layer Thickness (µm) | Beam Diameter (µm) | Scanning Speed (mms$^{-1}$) | Atmosphere | No. of Layers | Overlap (% of line width) |
|---|---|---|---|---|---|---|
| 78 | 100 | 100 | 100-260 | No | 16 | 25, 50, −500 |

The incremental changes in scanning speed and the size of the speed range were modified as the experiments progressed. To begin with, a large range of speeds was used to provide an initial indication of the material's performance and the propensity to melt. As the experiments progressed, the range was reduced to more closely define the process window. Speed and beam overlap variations were used to modify the specific energy density being applied to the powder bed and change the characteristics of the final structure. The complete series of parameters are given in FIG. 7, the parameters sets used for the definitive samples are shaded in gray.

The key laser parameters varied for forming the three-dimensional metallic porous structures are: (a) Laser scanning speed (v.) in (mms-1), which controls the rate at which the laser traverses the powder bed; (b) Laser power, P(W), which in conjunction with the laser spot size controls the intensity of the laser beam. The spot size was kept constant throughout the experiment; (c) Frequency, (Hz) or pulse repetition rate. This variable controls the number of laser pulses per second. A lower frequency delivers a higher peak power and vice versa.

The line width can be related to the laser scanning speed and the laser power to provide a measure of specific density, known as the "Andrew Number", where:

$$An = \frac{P}{bxv}(J/mm^{-2})$$

Where P denotes the power of the laser, v is the laser scanning speed and b denotes beam width of the laser. The Andrew number is the basis for the calculation of the present invention. The Andrew number may also be calculated by substituting the line separation (d) for beam width (b). The two methods of calculating the Andrew number will result in different values being obtained. When using line separation (d) as a factor only one track of fused powder is considered, whereas when using the beam width (b) as a factor, two tracks of fused powder are considered as well as the relative influence of one track to the next. For this reason we have chosen to concern ourselves with the Andrew number using scan spacing as a calculating factor. It can thus be appreciated, that the closer these tracks are together the greater the influence they have on one another.

Additionally, the laser power may be varied between 5 W and 1000 W. Utilizing lower power may be necessary for small and intricate parts but would be economically inefficient for such coatings and structures described herein. It should be noted that the upper limit of laser power is restricted because of the availability of current laser technology. However, if a laser was produced having a power in excess of 1000 W, the scanning speed of the laser could be increased in order that an acceptable Andrew number is achieved. A spot size having a range between 5 μm to 500 μm is also possible. For the spot size to increase while still maintaining an acceptable Andrew number, either the laser power must be increased or the scanning speed decreased.

The above formula gives an indication of how the physical parameters can vary the quantity of energy absorbed by the powder bed. That is, if the melted powder has limited cohesion, e.g. insufficient melting, the parameters can be varied to concentrate the energy supply to the powder. High Andrew numbers result in reduced pore coverage and an increase in pore size due to the effects of increased melt volume and flow. Low Andrew numbers result in low melt volume, high pore density and small pores. Current satisfactory Andrew numbers are approximately 0.3 J/mm-2 to 8 J/mm-2 and are applicable to many alternative laser sources. It is possible to use a higher powered laser with increased scanning speed and obtain an Andrew number within the working range stated above.

Figure 8A:
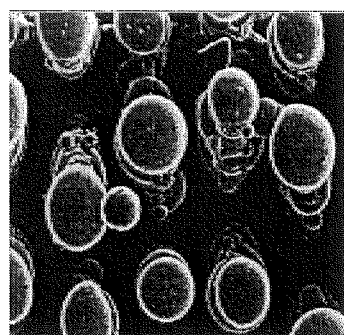
FIGS. 8A-8C are scanning electro-microscopic images of the surface structure of various samples made by a method according to the present invention.
Figure 8B:
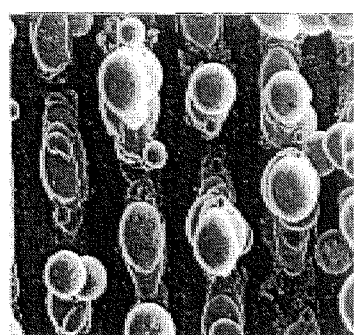
Figure 8C:
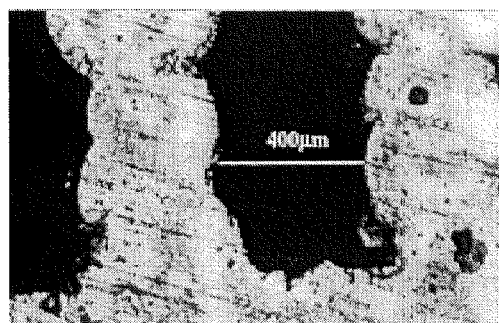

Line spacing or beam overlap can also be varied to allow for a gap between successive scan lines. It is, therefore, possible to heat selected areas. This gap would allow for a smaller or larger pore size to result. The best illustration of this is shown in FIGS. 8A to 8C where a −500% beam overlap has been applied. FIGS. 8A to 8C are scanning election microscope images of the surface structure of CoCr on stainless steel produced with a laser power of 82 W cw. FIG. 8A was produced with a laser scanning speed of 105 mms−1 and FIG. 8B was produced with a laser scanning speed of 135 mms−1. FIG. 8C is an image of the same structure in FIG. 8B, in section. There is a significant self-ordering within the overall structure. Larger columnar structures are selectively built leaving large regions of unmelted powder. It is worth noting that these pillars are around 300 μm wide, over 1.6 mm tall and fuse well with the substrate, as seen in FIG. 8C. Further analysis shows that the use of a hatched scanning format allows porosity to be more sufficiently controlled to allow the pore size to be directly controlled by the beam overlap.

The use of an optical inspection method to determine this approximate porosity is appropriate given the sample size. This method, although not accurate due to the filter selection process, can, if used carefully, provide an indication of porosity. This porosity level falls within the range of the desired porosity for bone ingrowth structures. The mechanical characteristics of the porous structures are determined by the extent of porosity and the interconnecting webs. A balance of these variables is necessary to achieve the mechanical properties required by the intended application.

Increased fusion may, if required, be obtained by heating the substrate, powder or both prior to scanning. Such heating sources are commonly included in standard selective laser sintering/melting/remelting machines to permit this operation.

As described above, the process can be carried out on flat baseplates that provide for easy powder delivery in successive layers of around 100 μm thickness. Control of powder layer thickness is very important if consistent surface properties are required. The application of this technology can also be applied to curved surfaces such as those found in modern prosthetic devices such as acetabular cup 10, with refinements being made to the powder layer technique.

The structures may receive ultrasonic and aqueous cleaning. On close examination, the resultant porous surfaces produced by the Direct Laser Remelting process exhibit small particulates that are scattered throughout the structure. It is unclear at this stage whether these particulates are bonded to the surface or loosely attached but there are means to remove or consolidate the particulates if required, by for example acid etching, heat treatment, a combination of the two, or the like.

The Direct Laser Remelting process has the ability to produce porous structures that are suitable for bone in-growth applications. The powdered surfaces have undergone considerable thermal cycling culminating in rapid cooling rates that have produced very fine dendritic structures.

The Direct Laser Remelting process can produce effective bone in-growth surfaces and the manufacturing costs are reasonable.

In the preceding examples, the object has been to provide a metal insert having a porosity on a base but the present invention can also be used to provide a non-porous structure on such a base to form a three-dimensional structure. The same techniques can be utilized for the materials concerned but the laser processing parameters can be appropriately selected so that a substantially solid non-porous structure is achieved.

Again, a technique can be used to deposit the powder onto a suitable carrier, for example a mold, and to carry out the process without the use of a base so that a three-dimensional structure is achieved which can be either porous, as described above, or non-porous if required.

It will be appreciated that this method can, therefore, be used to produce article from the metals referred to which can be created to a desired shape and which may or may not require subsequent machining. Yet again, such an article can be produced so that it has a graded porosity of, e.g., non-porous through various degrees of porosity to the outer surface layer. Such articles could be surgical prostheses, parts or any other article to which this method of production would be advantageous.

Although the porous structure has been discussed with regard to randomly depositing powder onto a substrate and selectively laser melting the powder while repeating layer after layer, in contrast, each layer or portion of a layer, may be scanned to create a portion of a plurality of predetermined unit cells. As successive layers of powder are deposited onto previous layers, the scanning and depositing of such layers continues the building process of a predetermined unit cell. When constructing the predetermined unit cells, the preferred embodiment includes employing a pulse high energy beam to form "spots" on the deposited powder layer. At least some of the "spots" are joined to produce struts or portions of struts, which constitute a portion of a predetermined unit cell. The spots may be created at random, in a continuous manner or a combination of the two. Examples of some possible geometric shapes of a unit cell are shown in FIGS. 9A-9D. As disclosed herein, by continuing the building process refers not only to a continuation of a unit cell from a previous layer but also a beginning of a new unit cell as well as the completion of a unit cell.

The invention can include a laser melting process that precludes the requirement for subsequent heat treatment of the structure, thereby preserving the initial mechanical properties of the core or base metal. The equipment used for the manufacture of such a device could be one of many currently available including the MCP Realiszer, the EOS M270, Trumpf Trumaform 250, the Arcam EBM S12 and the like. The laser may also be a custom produced laboratory device.

Figure 5:
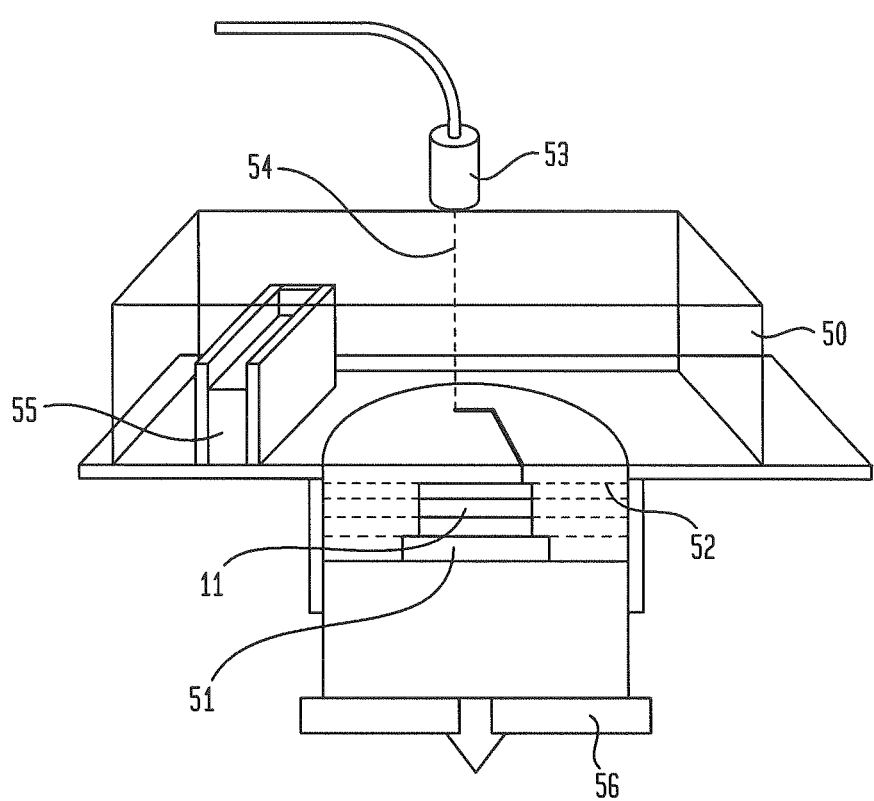
FIG. 5 illustrates an alternate apparatus for employing methods of the present invention.

As shown in FIG. 5, one apparatus for constructing a structure comprised of predetermined unit cells may include a chamber 50 filled with an inactive gas such as argon and nitrogen. By using an inactive gas you can avoid oxidation of the metal powder 52. The three-dimensional model, such as metal insert 11 may be built on a base plate 51. The model is built in a layer by layer fashion.

As successive layers of metal powder are deposited onto previous layers, the laser head 53 projects a beam of energy 54 onto locations of the powder to thereby form a spot or portion of a strut of a predetermined unit cell. The laser scans the powder bed and projects the energy beam based on the slice data of the model contained in the computer program.

After a layer has been completed, successive layer of metal powder may be deposited onto the previous layer by the use of a powder feeder 55. The powder feeder 55 may work in conjunction with a piston 56 that is lowered prior to the depositing of the additional layer of metal powder. The piston 56 is desirably positioned under the substrate on which the metal structure is built. As each layer is processed, the piston 56 may be lowered and an additional layer of metal powder deposited onto the previous layer. In this manner, each layer of unprocessed powder is positioned at the same distance from the laser head 53. The laser beam is capable of being directed along a X, Y coordinate system such that the desired location of the layer of metal powder can be engaged by the beam of energy 54. The guiding of the laser beam is dependent on the manufacturing system used. For example, if an E-beam system is employed the movement of the E-beam is controlled by deployment of the magnetic fields. If a laser beam apparatus is employed, the movement or guidance of the laser beam is controlled by a galvanometer.

The pore density, pore size and pore size distribution can be controlled from one location on the structure to another. It is important to note that successive powder layers can differ in porosity by varying factors used for laser scanning powder layers. Additionally, the porosity of successive layers of powder can be varied by either creating a specific type of predetermined unit cell or manipulating various dimensions of a given predetermined unit cell.

As described in U.S. patent application Ser. No. 11/027,421, the disclosure of which is incorporated by reference herein, such unit cells designs can be a tetrahedron 60 (FIG. 9A), dodecahedron 62 (FIG. 9B), octahedron 64 (FIG. 9C), diamond, as well as many other various shapes. In addition, various struts may be removed from a unit cell to create an additional structure such as that shown in FIG. 9D. Besides regular geometric shapes as discussed above, the unit cells of the present invention may be configured to have irregular shapes where various sides and dimensions have little if any repeating sequences. The unit cells can be configured to build constructs that closely mimic the structure of trabecular bone for instance. Unit cells can be space filling, all the space within a three-dimensional object is filled with cells, or interconnected where there may be some space left between cells but the cells are connected together by their edges. The unit cells can also be constructed in a form of a lattice. Additionally, adjacent lattices may be isolated from one another or only partially attached.

The cells can be distributed within the construct a number of ways. Firstly, they may be made into a block within a computer added design ("CAD") system where the dimensions correspond to the extent of the solid geometry. This block can then be intersected with the geometry representing the component to produce a porous cellular representation of the geometry. Secondly, the cells may be deformed so as to drape over an object thus allowing the cells to follow the surface of the geometry. Thirdly, the cells can be populated through the geometry following the contours of any selected surface.

The unit cell can be open or complete at the surface of the construct to produce a desired effect. For instance, open cells with truncated lattice struts produce a surface with a porosity and impart the surface with some degree of barb, whereas closed cells can be "peaky" so as to increase surface roughness.

Modifying the lattice strut dimensions can control the mechanical strength of the unit cell. This modification can be in a number of key areas. The lattice strut can be adjusted by careful selection of build parameters or specifically by changing the design of the cross-section of each strut. The density of the lattice can similarly be adjusted by modification of the density of the unit cells as can the extent and shape of porosity or a combination thereof. Clearly the overall design of the unit cell will also have a significant effect of the structural performance of the lattice. For instance, dodecahedral unit cells have a different mechanical performance when compared to a tetrahedral (diamond) structure.

Figure 9A:
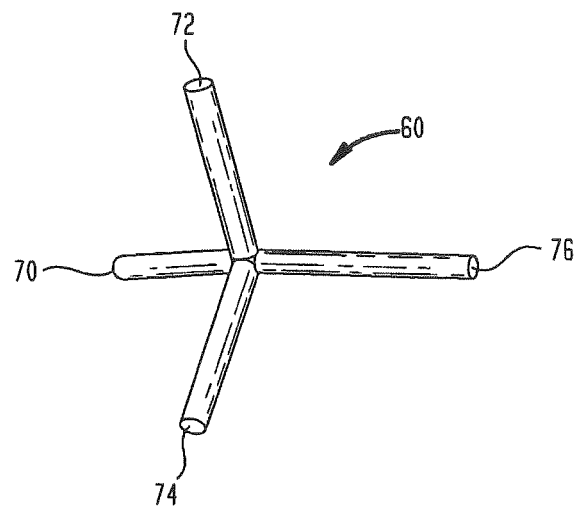
FIG. 9A-9D are illustrations of different embodiments of unit cells according to the present invention.

As shown in FIG. 9A, in a tetrahedron 60, each point 70, 72, 74, and 76 is the same distance from the neighboring point. This structure is analogous to the arrangements of carbon atoms in diamond.

Each carbon atom in the diamond structure is surrounded by four nearest neighbors. They are connected together by bonds that separate them by a distance of 1.5445 angstroms. The angles between these bonds are 109.5 degrees. As a result, the central atom and its neighbors form a tetrahedron. This geometry as in the case discussed herein may then be scaled to appropriate value for the pore construct required.

The two key parameters used to define the relations regarding height, surface area, space height, volume of tetrahedron, and the dihedral angle of a tetrahedron are the strand length of the tetrahedron and, i.e., the diameter or height and width, cross section area of the strand i.e., strut. These two parameters control the pore size and porosity of the structure. The parameter editor and relation editor within a typical CAD system can be used to control these parameters. Hence, by changing the parameters one can change the fundamental properties of the porous structure. As shown in FIG. 9A, the diamond structure may have a circular cross-section strands or square cross-section strands. Although only two strand cross-sections are discussed herein, strands having various cross-sections are possible. Further, this is true with most of the designs for the unit cell.

Figure 10:
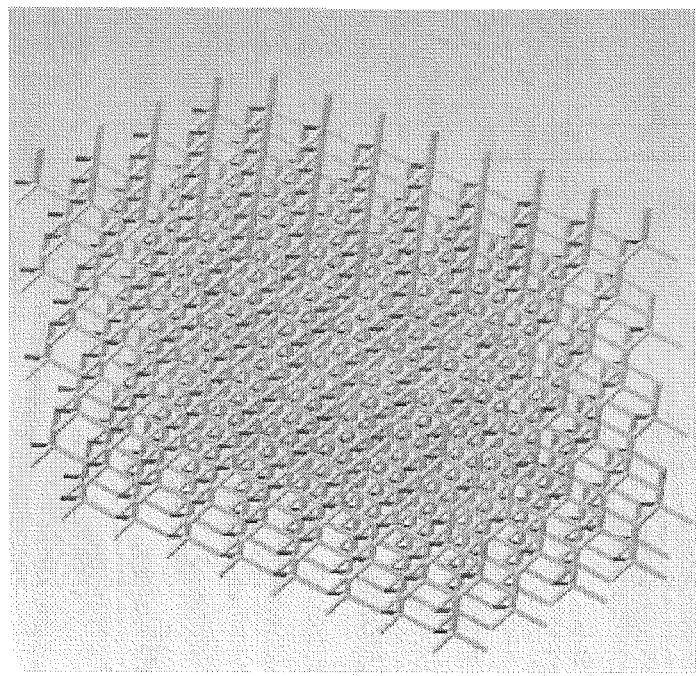
FIG. 10 illustrates a lattice structure using a plurality of unit cells according to FIG. 8A.
Figure 11:
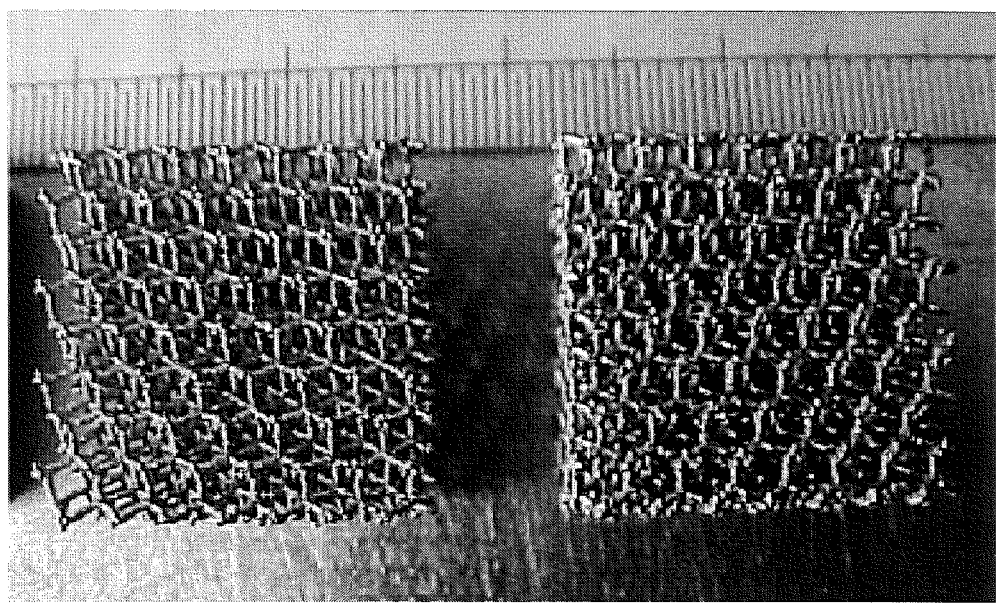
FIG. 11 illustrates a lattice structure with and without laser beam compensation using the unit cells illustrated in FIG. 1.

To create the mesh as shown in FIG. 10, the unit cell can be instanced across the 3-D space to produce the required lattice. FIG. 11 illustrates a view of a diamond lattice structure with and without laser beam compensation. Laser beam compensation essentially allows the diameter of the beam to be taken into account. Without it the constructed geometry is one beam diameter too wide as the beam traces out the contour of the particular section being grown. When laser beam compensation is utilized, the contour is offset half a beam diameter all around the constructed geometry which is represented in the CAD file. Although various parameters may be used, the parameters employed to create the lattices of FIG. 11 include a laser power of 90.5 watts with an exposure time of 1,000 μsec from a point distance of 90 μm. Table 3 illustrates various other examples of parameters that may be used to create various unit cells.

TABLE 3

| Part build on SLM | edge length μm | diameter μm | laser power Watts | exposure μsec | point distance μm |
|---|---|---|---|---|---|
| Diamond Structure | 2000 | 200 | 90.5 | 1000 | 90 |
| Diamond Structure with compensation | 2000 | 200 | 90.5 | 1000 | 90 |
| Dodecahedron Structure | 1500 | 200 | 68.3 | 1000 | 90 |
| Dodecahedron Structure with compensation | 1500 | 200 | 68.3 | 1000 | 90 |
| Modified Truncated Octahedron | 1500 | 200 | 90.5 | 1000 | 90 |

Figure 9B:
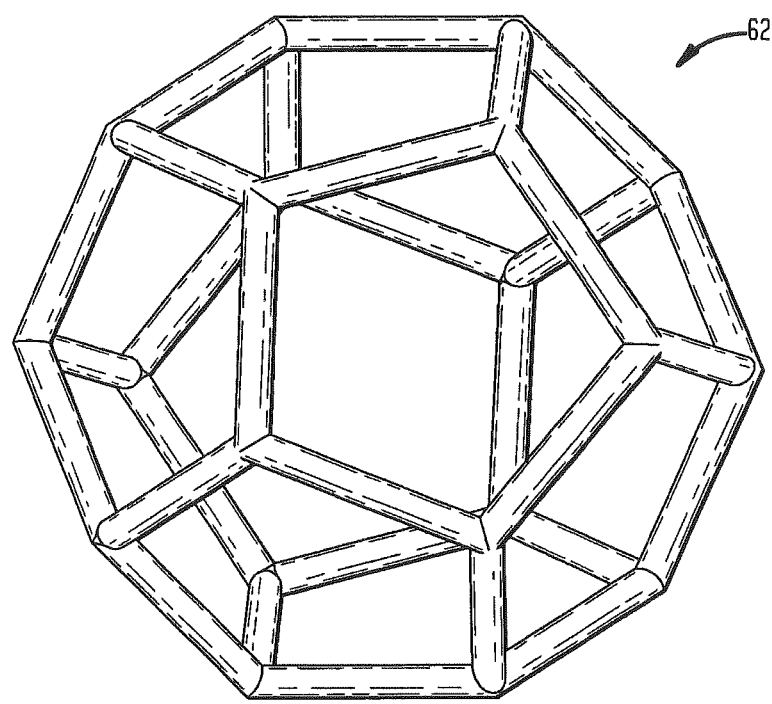
Figure 12:
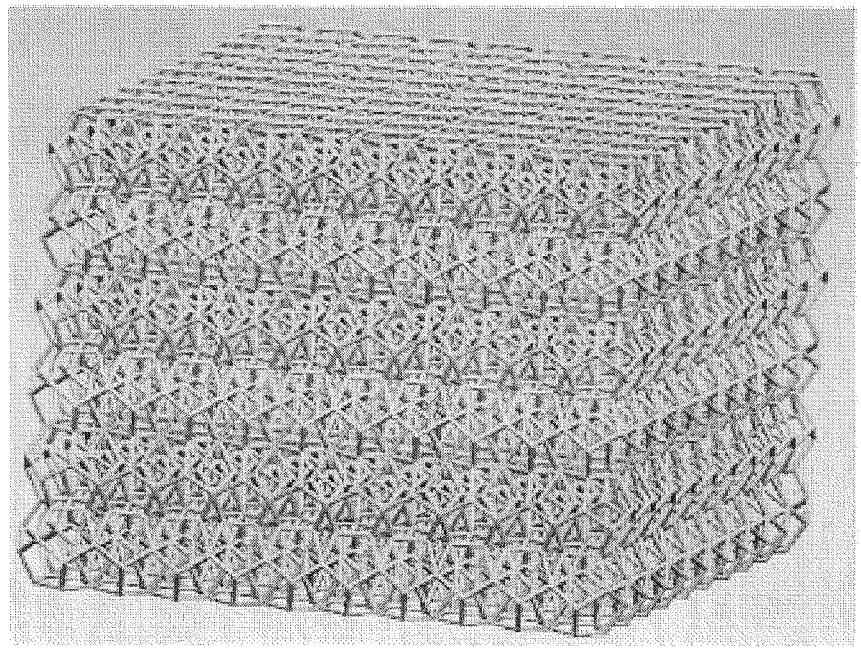
FIG. 12 illustrates a lattice structure using a plurality of unit cells illustrated in FIG. 8B.

As shown in FIGS. 9B and 12, the porous structure can also be created using a unit cell in the shape of a dodecahedron. The regular dodecahedron is a platonic solid composed of 20 polyhydron vertices, 30 polyhydron edges, and 12 pentagonal faces. This polyhydron is one of an order of five regular polyhedra, that is, they each represent the regular division of 3-dimensional space, equilaterally and equiangularly. This basic unit cell for a decahedron mesh can be built up in a CAD package using the following calculations and procedure. The dodecahedron has twelve regular pentagonal faces, twenty vertices, and thirty edges. These faces meet at each vertex. The calculations for a side length of a dodecahedron are given by simple trigonometry calculations and are known by those in the art.

In a method of use, a sweep feature is first used to model the dodecahedron structure by driving a profile along a trajectory curve. The trajectory curves are constructed from datum points corresponding to the vertices of the dodecahedron connected by datum curves. The type of profile remains constant along the sweep producing the model shown in FIG. 9B. The size and shape of the profile can be designed to suit the particular application and the required strut diameter. Once a particular unit cell has been designed, the cell can be instanced to produce a regular lattice as shown in FIG. 12. As a dodecahedron is not spaced filling, meshes are produced by simple offsetting of the unit cell and allowing some of the struts to overlap. This method of overlapping may be used with the alternate shapes of the unit cell.

Figure 13:
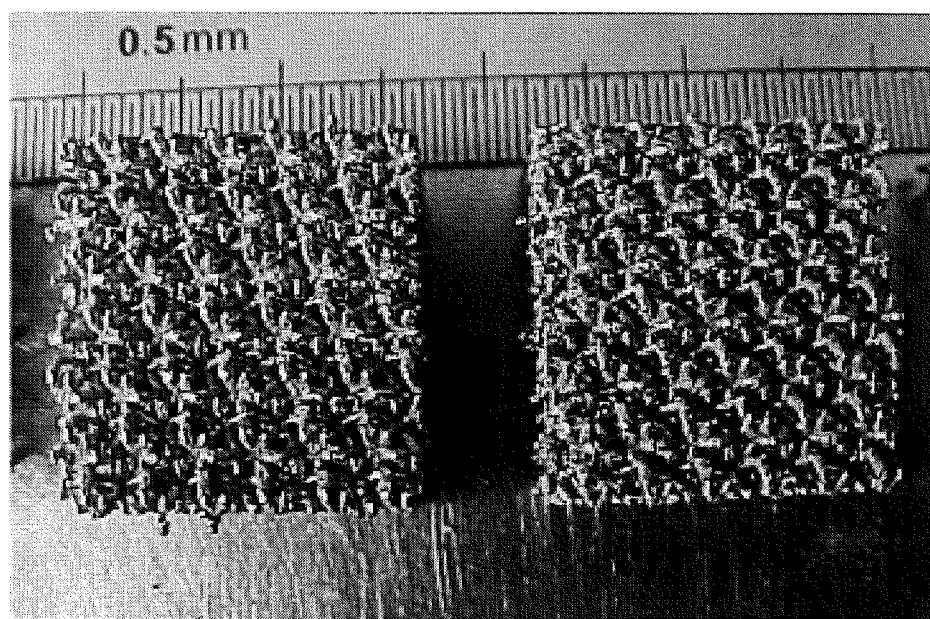
FIG. 13 illustrates a lattice structure with and without laser beam compensation using the unit cell of FIG. 8B.

FIG. 13 shows a view of a dodecahedron (with and without laser beam compensation, from left to right) structure using selective laser melting process parameters. Once again, although the parameters may be varied, the lattices of FIG. 13 were created using the following parameters; a laser power of 90.5 watts, exposure of the powder for 1,000 usec and a point distance of 90 μm.

Figure 9C:
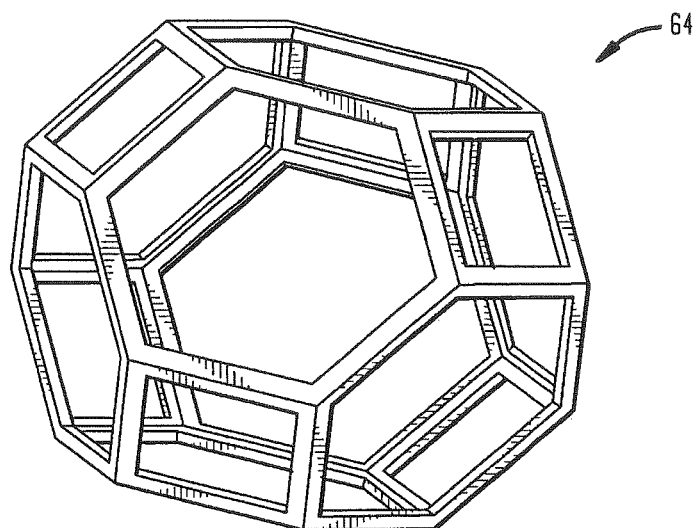
Figure 14:
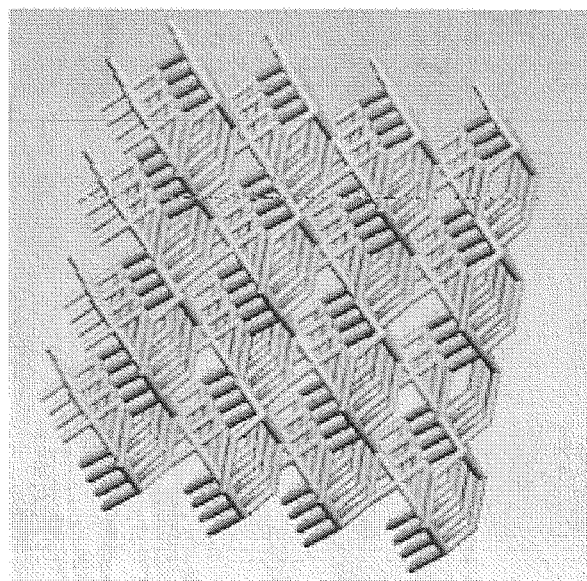
FIG. 14 illustrates a lattice structure using a plurality of unit cells illustrated in FIG. 8C.

As shown in FIGS. 9C and 14, the unit cell of the present invention may also be constructed in the shape of a truncated octahedron. A truncated octahedron has eight regular hexagonal faces, six regular square faces, twenty-four vertices, and thirty-six edges. A square and two hexagons meet at each vertex. When the octahedron is truncated, it creates a square face replacing the vertex, and changes the triangular face to a hexagonal face. This solid contains six square faces and eight hexagonal faces. The square faces replace the vertices and thus this leads to the formation of the hexagonal faces. It should be noted here that these truncations are not regular polydra, but rather square-based prisms. All edges of an archamedian solid have the same length, since the features are regular polygons and the edges of a regular polygon have the same length. The neighbors of a polygon must have the same edge length, therefore also the neighbors and so on. As with previous unit cells, various dimensions such as the octahedron height, octahedron volume, octahedron surface area, octahedron dihydral angle, and truncated octahedron volume, truncated octahedron height, truncated octahedron area, truncated octahedron volume, truncated octahedron dihydral angle can be determined by simple trigonometry and are known by those skilled in the art.

Figure 9D:
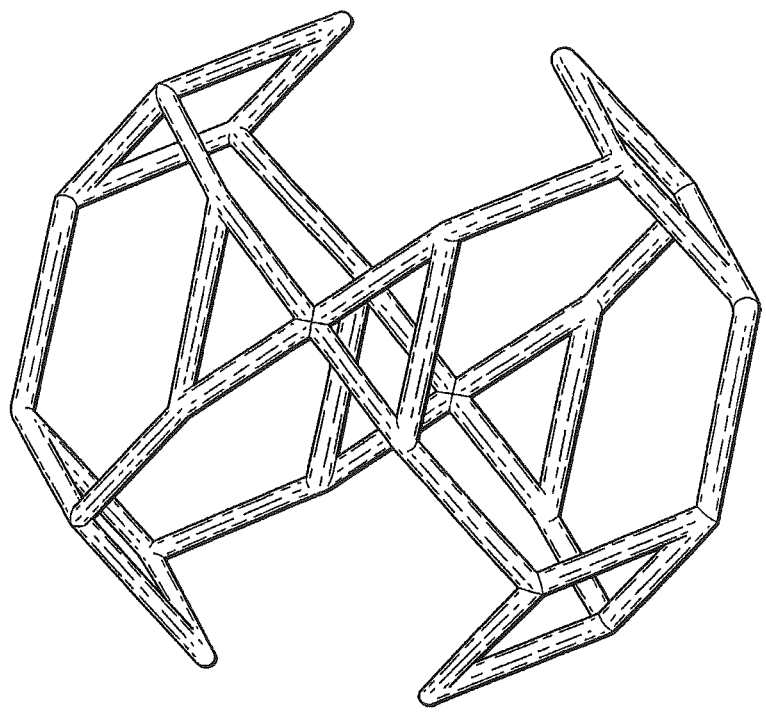

In a method of use, a CAD model of the truncated octahedron is constructed using the sweep feature and calculations and dimensions are incorporated using basic trigonometry. To tessellate the unit cell, the unit cell is first reoriented to enable easy tessellation and to reduce the number of horizontal struts in the model. Further, the model can be modified to remove all of the horizontal struts as shown in FIG. 9D. The modified structure is reproduced in order to save file size in the Steriolithography ("STL") format of the program. Next, in order to create the unit cells, the method of using a laser melting process is performed. In one preferred embodiment, the parameter chosen includes a laser power of 90.5 watts, an exposure of 1000 μsec with a point distance of 90 μm. FIG. 8B illustrates a lattice structure formed using a plurality of individual truncated octahedron. As discussed earlier, the removal of various struts can create a barb effect on the exterior surface of the lattice structure.

Figure 15A:
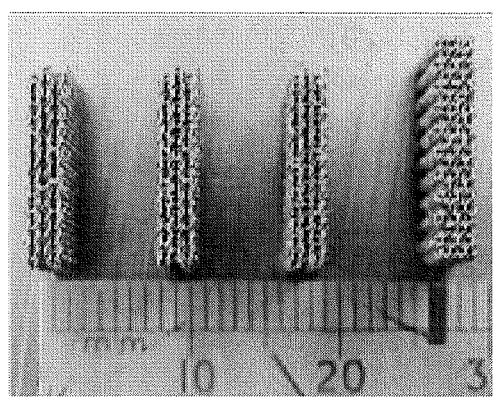
FIGS. 15A and 15B illustrate lattice structures created using unit cells illustrated in FIGS. 9D and 8A with varying exposure time, respectively.
Figure 15B:
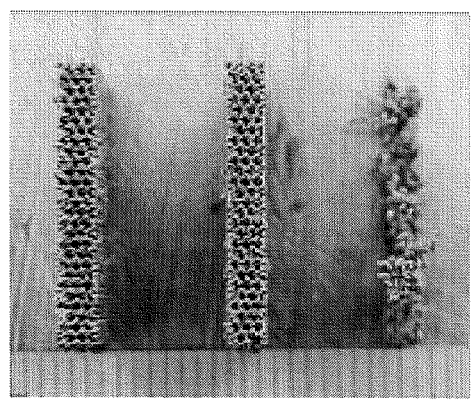
Figure 15C:
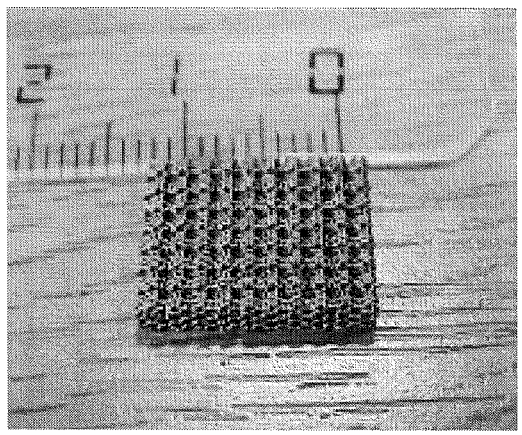
FIG. 15C illustrates a side view of the embodiment of FIG. 15A.
Figure 15D:
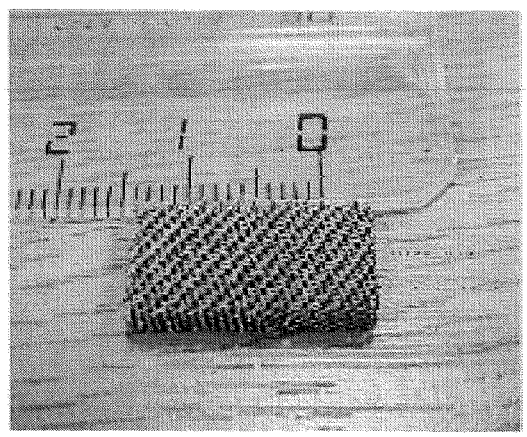
FIG. 15D illustrates a side view of the lattice structure illustrated in FIG. 15B.

As shown in FIGS. 15A-D, it is possible to reduce the size of the unit cell geometry. Also as shown, it is possible to manufacture open cell structures with unit cell sizes below 1 millimeter. FIG. 15A illustrates truncated octahedron structures manufactured using the laser melting process. All the structures were created using a laser power of 90.5 W, and a point distance of 90 μm; however, from left to right, the exposure time was varied from 500 usec and 100 μsec. FIG. 15 illustrates similar structures and parameters as used with FIG. 15A, however, the unit cell used to create the lattice is diamond. FIGS. 9C and 9D illustrate a side view of the truncated octahedron structure of FIG. 15A and the diamond structure of FIG. 15B, respectively. Table 4 includes various manufacturing parameters used to construct various unit cell structure.

TABLE 4

| Part build on SLM | Strand length μm | Length of strand c/s μm | Width of strand c/s μm | Laser Power Watts | Exposure μsec | Point distance μm |
|---|---|---|---|---|---|---|
| Truncated Octahedron | 3000 | 50 | 50 | 90.5 | 500 | 90 |
| Truncated Octahedron | 3000 | 50 | 50 | 90.5 | 300 | 90 |
| Truncated Octahedron | 3000 | 50 | 50 | 90.5 | 100 | 90 |

TABLE 4-continued

| Part build on SLM | Strand length μm | Length of strand c/s μm | Width of strand c/s μm | Laser Power Watts | Exposure μsec | Point distance μm |
|---|---|---|---|---|---|---|
| Truncated Octahedron | 1000 | 50 | 50 | 90.5 | 500 | 90 |
| Truncated Octahedron | 1000 | 50 | 50 | 90.5 | 300 | 90 |
| Truncated Octahedron | 1000 | 50 | 50 | 90.5 | 100 | 90 |
| Diamond Structure | 700 | 50 | 50 | 90.5 | 500 | 90 |
| Diamond Structure | 700 | 50 | 50 | 90.5 | 300 | 90 |
| Diamond Structure | 700 | 50 | 50 | 90.5 | 100 | 90 |

Figure 16:
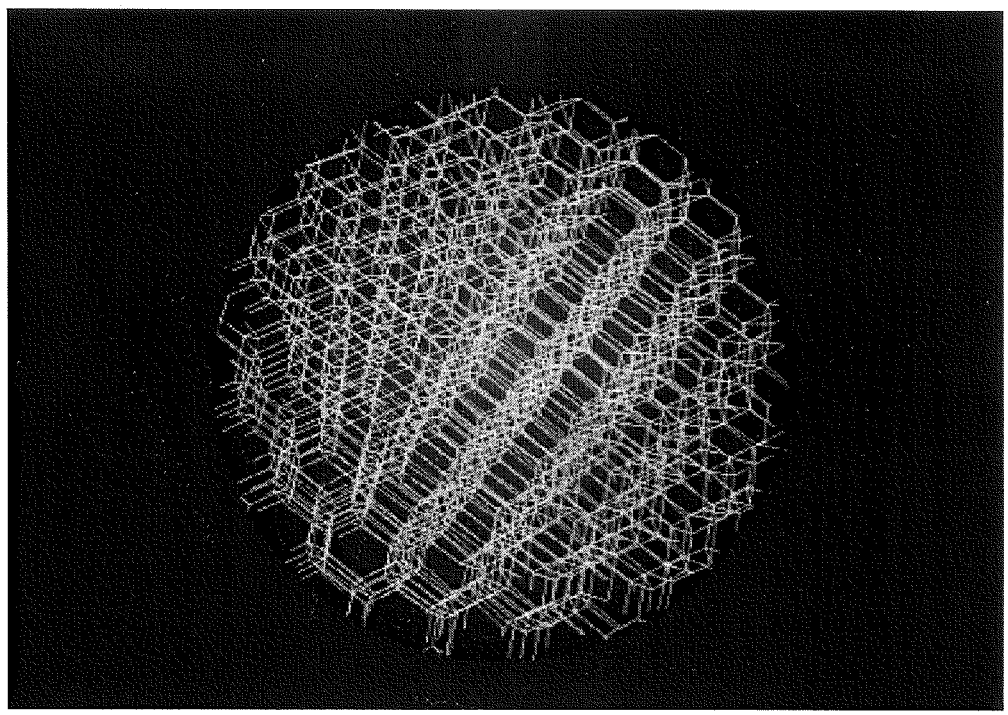
FIG. 16 is a representation of a lattice structure created using a plurality of unit cells illustrated in FIG. 8D with random perturbation.

Pseudorandom representative geometries may be made from the current regular unit cells by applying a random X, Y, Z perturbation to the vertices of the unit cells. One such example can be seen in FIG. 16. In another aspect of the present invention, various freestanding constructs can be generated.

Various other methods may also be utilized to produce the bone ingrowth structure 14, bearing support structure 12 and/or the intermediate structure 16 of the acetabular cup 10 in methods known to those in the art.

In one preferred embodiment, the average pore size of the bone ingrowth structure 14 falls within 280 μm to 480 μm, as measured using conventional linear intercept methods. A bimodal pore size distribution may be present as, for example, small pores within a 250 μm to 450 μm range and larger pores within a 600 μm to 800 μm range. The metal insert 11, i.e., the bone ingrowth structure 14, the bearing support structure and the intermediate structure 14 may be isotropic as, for example, without directionality with regard to the structure, and mechanical properties.

In one preferred embodiment, the average pore sizes of the porous layer 14 for interconnecting pores exceeds 250 μm with at least 99% and the pore volume therefore within between 65% to 75% of interconnecting pores exceeding 180 μm.

The general thickness of the porous layer generally lies within the range of between 1 mm to 2 mm but may be larger or smaller if so required.

The porous structure 14, bearing support structure 12 and the intermediate structure 16 may be formed simultaneously using any of the processes described herein or a combination of the processes.

Once the metallic structure has been formed, e.g., the bone ingrowth, bearing and intermediate structures, a polymeric material may be connected to the bearing support structure 12 to enable the acetabular cup 10 to bear against an articulating surface of an additional element. The polymeric material will comprise the bearing surface 8 of the acetabular cup 10

Depending on the material used to create the bearing surface 8, the polymeric material can be integrated with the bearing support structure 12, by compression molding, injection molding or heat forming. It may also be possible to cast certain types of materials from solution as, for example, polyurethane.

If the polymeric material used to form the bearing surface 8 is an ultra-high molecular weight polyethylene ("UHMWPE") material or the like, the metallic insert, i.e., the bone ingrowth structure 14, the bearing support structure 12 and the intermediate structure 16, but specifically the bearing support structure 12, may be joined to the bearing surface 8 by a compression molding process using a matched metal die. The metal insert 11 is placed into a cavity part of a metal die. The polymer powder may then be added to the cavity of the metal die and desirably is dispersed against the bearing support structure 12. The cavity of the metal die is sealed and the metal die is then heated to a required temperature. As the temperature of the polymer powder is increased, the polymer powder begins to soften or melt so as to be flowable. Increased pressure onto the polymer powder may also aid in the melting process. Fusion of the polymer powder and attachment to the bearing support structure 12 is achieved when the acquired application of heat and pressure is reached. Subsequent cooling under pressure allows solidification of the polymer powder, which thus forms the bearing surface 8 that is securely attached to the bearing support structure 12. A final machining operation may be required to complete the construct of the bearing surface 8.

In one preferred embodiment, the metal insert 11 is situated in the metal die with the bone ingrowth structure 14 bounded within the cavity of the metal die such that the polymer material cannot come in contact with the bone ingrowth structure. And since the intermediate structure 16 is preferably substantially solid, the intermediate structure prohibits or at least, reduces the ability of the polymeric material to come in contact with the bone ingrowth structure as the polymeric material attaches to the bearing support structure 12 to form a bearing surface 8. By keeping the pores of the bone ingrowth structure unencumbered with polymer material, the ability of the bone ingrowth structure to promote bone ingrowth is not altered.

In an alternate embodiment, an injection molding process may be carried out in order to fuse the bearing surface 8 to the bearing support structure 12. An injection molding process may be preferred when the material used to create the bearing surface 8 is a polyurethane or chopped-fiber-reinforced poly (ETHERETHERKETONE) ("CFRPEEK"). Similar to the compression molding process, in the injection molding process, the metal insert 11 is secured into a cavity of an injection molding machine and the mold closed. As with the previous embodiment, the bone ingrowth structure 14 may be isolated from the polyurethane or additional polymer used. The selected material, e.g., polyurethane or CFRPEEK is heated in a barrel of the injection molding machine. Once the selected material is heated in the barrel of the injection mold, the pressure may be applied to the selected material to urge the heated selected material from the barrel into the mold cavity and onto a surface of the bearing support structure 12. Upon cooling, the selected material is fused to the bearing support structure 12 so as to form the bearing surface 8 upon which the acetabular cup 10 may move relative to an additional element, i.e., the femoral stem FS. Upon cooling, the completed part may be removed from the injection mold and machined if so required. The mold cavity can be configured such that particular features, designs and contours of the bearing surface 8 may be formed.

In still yet another alternate embodiment, the bearing surface 8 may be formed using a heat forming process. In a heat-forming process, materials such as UHMWPE are supplied as fabricated rod stock suitable for machining. Profiles can be produced by machining the fabricated rod stock to represent a near net shape of the intended article such as the bearing surface 8 of the acetabular cup 10. Once the article has been produced, both the metal insert 11 and the shape polymer machine part are placed into a mold and heated to the required temperature. Upon the application of heat and pressure, the softened polymer is forced into and against the metal insert 11, specifically the bearing support structure 12. Upon cooling, solidification takes place and the polymer is secured to the metal insert 11 and specifically the bearing support structure 12. Further machining may be required if necessary once the part has been allowed to cool and is removed from the mold.

As with previous embodiments, in combination with the intermediate structure 16 and additional elements, the bone ingrowth structure 14 may be isolated from any polymeric material so that the polymeric material cannot affect the ability of the structure to promote bone ingrowth.

In yet still another alternate embodiment, the bearing surface 8 may be constructed using a solution casting method. In a solution casting method, a material, such as a polyurethane material, can be formed by casting solvent-dissolved solutions in the mold.

In addition to the method as described above, it is also possible to make the bearing surface 8 out of additional material such as a metallic material or ceramic material. As such, when forming the bearing surface 8 from a metallic material, the selective laser melting process, described herein, as well as in U.S. patent application Ser. Nos. 10/704,270, and 11/027,421 (described above) may be utilized.

An example of a process for forming the acetabular cup 10 is discussed herein, although various methods may be employed. In a preferred method, software and equipment, as shown in Table 6 below, may be employed to build a finished product.

TABLE 6

| Equipment/Software | Description |
| --- | --- |
| MCP realiser | SLM machine using 100 w fibre laser |
| Magics V8.05 (Materialise) | CAD software package used for manipulating STL files and preparing builds for Rapid Manufacture (RM) |
| Manipulator 3.4.1 | Propriety program for populating a solid STL file with porous surface coating. Outputs a sliced F&S file ready for manufacture |
| Fusco | MCP realiser operating software |
| Gas atomized co - titanium powder | Metal powder with a mean particle size of approximately 40 µm |

Figure 17:
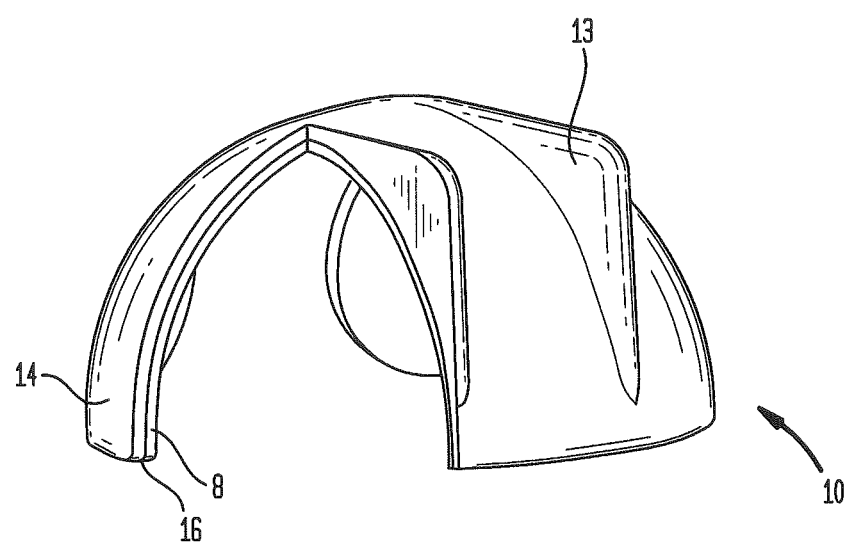
FIG. 17 is an illustration of an acetabular cup built using the methods of the present invention.

In a first step of such process, a CAD file of an acetabular cup component is loaded into the Magics software package as a single part, as shown in FIG. 17. The file may then be divided into three separate solid volumes having a 1.1 mm thick outer layer—this layer will be used to create the 80% porous bone ingrowth surface; 0.1 mm thick intermediate layer—this layer will be a fully dense layer that supports the bone ingrowth surface; and 0.8 mm thick inner layer—this will be used to create an interlock surface for a polymer injection molding. The three layers, when completed, will comprise the metal insert 11 of the acetabular cup 10.

A completed acetabular cup 10 is shown is shown in FIG. 17 and includes a bearing surface 8, an intermediate structure 16 and a bone ingrowth structure 12. The bone ingrowth structure 14 may include fins or protrusions 13 for anchoring into bone.

Figure 18:
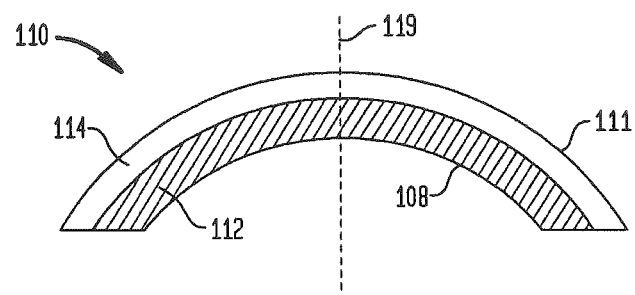
FIG. 18 is an illustration of an alternate embodiment of an acetabular cup built using the methods of the present invention.

In an alternate embodiment of the present invention, the acetabular cup may be constructed with a two tier structure. As shown in FIG. 18, which is a cross section of an acetabular cup 110, the two tier structure includes a metal insert 111 having a bone ingrowth structure 114 and a bearing support structure 112. The bearing surface 108 is attached to the bearing support structure 112 are connected directly to one another. But each structure is adapted for its own purpose, i.e., the bone ingrowth structure 14 has a porosity adapted for bone ingrowth and the bearing support structure 12 has a porosity suited for anchoring a polymeric material or additional material as discussed herein.

Although the figure illustrates a demarcation between the two structures, highlighting the difference in porosity between the two, the actual metal insert 111 may have a graded porosity which increases, decreases or some combination of the two along an axis 119 passing through the center of the acetabular cup 110.

Figure 19:
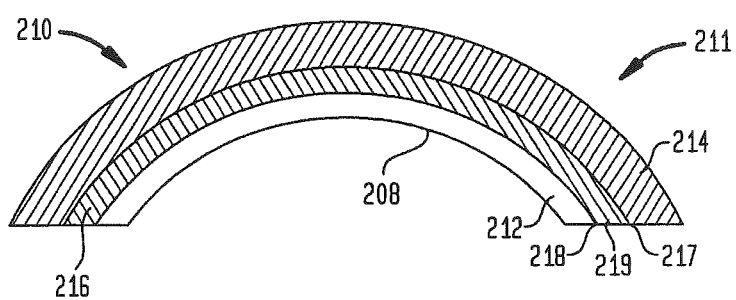
FIG. 19 is an illustration of an alternate embodiment of an acetabular cup built using the methods of the present invention.

In yet another alternate embodiment, as shown in FIG. 19, the acetabular cup 210 may have a plurality of structures comprising a metal insert 211. The metal insert 211 may include a bone ingrowth structure 214, an intermediate structure 216 and a bearing support structure 212. The intermediate structure 216 may include a first barrier 217, a second barrier 218 and a bridging structure 219. The first barrier 217 and second barrier 218 may be substantially solid while the bridging structure 219, positioned between the two barriers has a particular porosity. The particular porosity may be specifically designed to transfer mechanical loads through the overall construct to a bone to which the acetabular cup is attached to. Once the metal insert 211 is designed, the bearing surface 208 may be coupled thereto as described herein.

Figure 20:
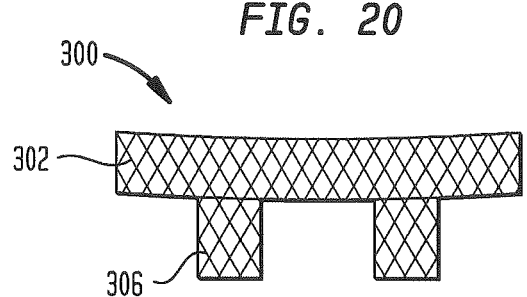
FIGS. 20 and 21 are representations of a patella component built using one embodiment of the present invention.
Figure 21:
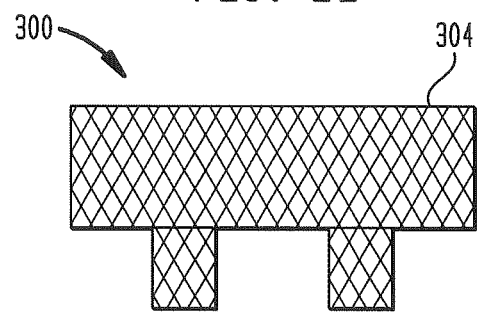

Although the present invention has been discussed with regard to constructing an acetabular cup, various other orthopedic implants, tools, apparatus, and structures may also be built using the same process. For instance, a patella component 300, as shown in FIGS. 20 and 21, includes a baseplate 302 and a bearing surface 304.

As with the acetabular cup discussed herein, once the baseplate 302 had been constructed, the patella bearing surface 304 may be attached to the baseplate 302 using the processes discussed herein.

In a method of assembly, the patella is shaved on a posterior side to a desired depth and some of the cartilage surrounding the area is removed. The baseplate 302 of the patella component preferably includes a plurality of pegs 306 that engage the remaining bone of the patella. The pegs 306 are designed for bone ingrowth as discussed in here. With the pegs 306 attached to the posterior of the patella, the bearing surface 304 may replace and perform the function of any cartilage removed from the area.

Figure 22:
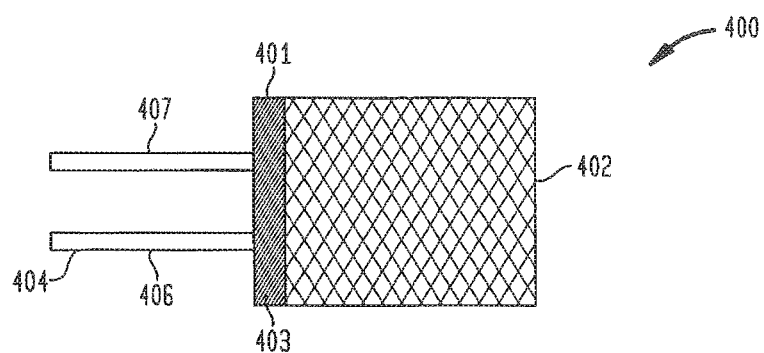
FIG. 22 is a side view of a cartilage plug built according to one embodiment of the present invention.
Figure 23:
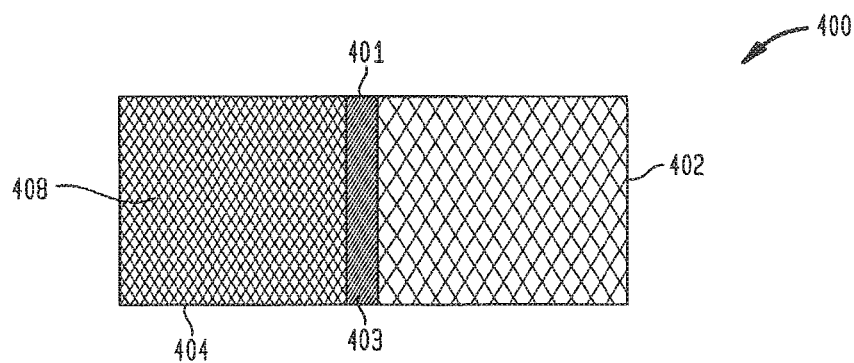
FIG. 23 is a front view of the cartilage plug of FIG. 22.

In yet another alternate embodiment, as shown in FIGS. 22 and 23, the present invention can be used to construct a cartilage plug 400. The cartilage plug 400 desirably includes a metal insert 401 having a bone ingrowth structure 402, an intermediate structure 403 and a bearing support structure 404. The metal insert 401 may be constructed using methods discussed herein. Once the metal insert 401 is completed, the bearing surface 408 may be attached to the bearing support structure 404 as discussed herein.

For illustration purposes, the bearing support structure 404 is comprised of two independent lattices 406 and 407. The lattices 406 and 407 are independent from one another and may be constructed differently from each other. In alternate embodiments, the bearing support structure 404 may be constructed similar to the bearing support structure 12 of the metal insert 11, discussed herein.

The cartilage plug 400 may be employed as for example when only a portion of a tibial plateau must be replaced. A bore is created in the tibial plateau removing the defective portion and than filled with the cartilage plug 400. The bone ingrowth structure 514 of the cartilage plug 400 is positioned within the bone while the bearing surface 408 faces outward to replace any cartilage removed from the area.

In yet another alternate embodiment not shown in the figures, the intermediate structure of an implant may be constructed using a die cast or any method known to those in the art. The resultant intermediate structure may then be placed onto the base plate of an apparatus similar to that shown in FIG. 4 or 5. Once in place, a bone ingrowth structure and bearing support structure may be built onto the intermediate structure.

As previously discussed, a bearing surface may be attached to an implant or metal insert indirectly. For example, as shown in FIG. 24, a metal insert 511 may be constructed similar to metal insert 11 in the shape of an acetabular cup 510, and include a bone ingrowth structure 514, an intermediate structure 516 and a bearing support structure 512. A bone cement 506 may be deposited and attached to the bearing support structure 512, in methods known to those in the art. A UHMWPE liner 509 is positioned adjacent the bone cement and is subsequently attached thereto as the bone cement polymerizes. The liner 509 preferably includes an exterior 502 and an interior 503. The exterior 502 of the liner 509 preferably includes a plurality of attachment sites such as radial grooves or as shown in the figure, circumferential grooves 504. As the liner 509 is forced against the bone cement the bone cement engages the grooves. As the bone cement 506 polymerizes, the liner 509 is mechanically interlocked to the bone cement.

The interior 503 of the liner 509 is suitable to act as a bearing surface of the completed acetabular cup 510. Preferably, the metal insert 511 and liner 509 are prepackaged and available to a surgeon in a plurality of sizes such that during surgery the surgeon only has to remove the desired liner and insert once the specific measurements and requirements have been decided upon.

Systems incorporating the used of a liner cemented to a porous metal insert are normally used when the acetabullum has been severely damaged or in some cases of revision surgery.

Although not shown in the figures, the present invention may be in the shape of a glenoid or any other component where bone ingrowth is desired in combination with a bearing surface.

As with all of the embodiments herein, it is possible to apply a coating of a bone growth enhancer as, for example, hydroxyapatite, bone morphogenic protein such as OP-1 (Stryker), to the surface intended to be in direct contact with bone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of fabricating a medical implant comprising the steps of:
   successively depositing layers of a material and at least partially melting at least a portion of each deposited layer of the material at predetermined locations to form a first porous portion of the implant surrounding perimeters of both a first solid section of the implant and a second solid section of the implant spaced from the first solid section.

2. The method of claim 1, wherein the implant is porous between the first solid section and the second solid section.

3. The method of claim 1, wherein the steps of successively depositing layers of a material and at least partially melting at least a portion of each deposited layer of the material at predetermined locations further forms a second porous portion of the implant between the first solid section and the second solid section.

4. The method of claim 1, wherein the first porous portion includes irregularly shaped pores.

5. The method of claim 4, wherein the irregularly shaped pores are defined by struts.

6. The method of claim 1, wherein the second solid section extends from a substrate.

7. The method of claim 6, wherein the substrate is a further porous portion of the implant.

8. The method of claim 1, wherein the first porous portion is defined by struts.

9. The method of claim 1, wherein the first porous portion is defined by tessellated cells, each cell being formed of struts including a first plurality of struts defining a first plane and a second plurality of struts sharing a strut with the first plurality of struts and defining a second plane transverse to the first plane.

10. The method of claim 1, wherein the first porous portion of the implant is formed surrounding a structure having a circular cross-section.

11. The method of claim 1, wherein the first solid section has a circular cross-section circumferentially surrounded by the first porous portion.

12. The method of claim 11, wherein the second solid section has a circular cross-section circumferentially surrounded by the first porous portion.

13. A method of fabricating a medical implant comprising the steps of:
   successively depositing layers of a material and at least partially melting at least a portion of each deposited layer of the material at predetermined locations to form a first porous portion of the implant surrounding perimeters of both a first solid section of the implant and a second solid section of the implant spaced from the first solid section,
   wherein the implant is porous between the first solid section and the second solid section, and
   wherein the first porous portion includes irregularly shaped pores.

14. The method of claim 13, wherein the second solid section extends from a substrate.

15. The method of claim 14, wherein the substrate is a further porous portion of the implant.

16. The method of claim 13, wherein the first solid section has a circular cross-section circumferentially surrounded by the first porous portion.

17. The method of claim 16, wherein the second solid section has a circular cross-section circumferentially surrounded by the first porous portion.

18. A method of fabricating a medical implant comprising the steps of:
- successively depositing layers of a material and at least partially melting at least a portion of each deposited layer of the material at predetermined locations to form a first porous portion of the implant surrounding perimeters of both a first solid section of the implant and a second solid section of the implant spaced from the first solid section,
- wherein the steps of successively depositing layers of a material and at least partially melting at least a portion of each deposited layer of the material at predetermined locations further forms a second porous portion of the implant between the first solid section and the second solid section,
- wherein the first porous portion includes irregularly shaped pores.

19. The method of claim 18, wherein the second solid section extends from a substrate.

20. The method of claim 19, wherein the substrate is a further porous portion of the implant.

\* \* \* \* \*